(12) United States Patent
Greaves et al.

(10) Patent No.: US 8,906,865 B2
(45) Date of Patent: Dec. 9, 2014

(54) TREATMENT OF INFLAMMATION AND/OR ENDOTOXIC SHOCK

(75) Inventors: David R. Greaves, Oxford (GB); Andreas Russ, Oxford (GB); Jenna L. Cash, London (GB)

(73) Assignee: ISIS Innovation Limited, Oxford (GB)

( * ) Notice: Subject to any disclaimer, the term of this patent is extended or adjusted under 35 U.S.C. 154(b) by 1022 days.

(21) Appl. No.: 12/532,365

(22) PCT Filed: Mar. 25, 2008

(86) PCT No.: PCT/GB2008/001020
§ 371 (c)(1), (2), (4) Date: Feb. 1, 2010

(87) PCT Pub. No.: WO2008/114037
PCT Pub. Date: Sep. 25, 2008

(65) Prior Publication Data
US 2010/0150990 A1    Jun. 17, 2010

(30) Foreign Application Priority Data

Mar. 22, 2007 (GB) .................................. 0705488.5

(51) Int. Cl.
*C07K 14/47* (2006.01)
*A61K 38/00* (2006.01)
*A61K 47/42* (2006.01)

(52) U.S. Cl.
CPC ................. *C07K 14/47* (2013.01); *A61K 38/00* (2013.01); *Y10S 514/886* (2013.01)
USPC ....... 514/21.4; 424/78.05; 424/445; 424/447; 514/1.1; 514/21.5; 514/21.6; 514/886; 530/326; 530/327

(58) Field of Classification Search
None
See application file for complete search history.

(56) References Cited

U.S. PATENT DOCUMENTS

2005/0202029 A1    9/2005   Zabel et al.

FOREIGN PATENT DOCUMENTS

WO    WO2005000875    *    1/2005

OTHER PUBLICATIONS

Lazar et al Mol. Cell. Biol., 1988, vol. 8, pp. 1247-1252.*
Wells, Biochemistry 1990, 29:8509-8517.*
Wittamer et al, The Journal of Biological Chemistry, 2004, vol. 279, No. 11, pp. 9956-9962.*
Wittamer et al, J. Exp. Med, 2003, vol. 198, No. 7, pp. 977-985.*
Wittamer et al, Journal of Immunology, 2005; vol. 175, No. 1, pp. 487-493.*
Cuzzocrea et al. European Cytokine Network, 1999, vol. 10, No. 2, pp. 191-204.*
Kulig et al., "*Staphylococcus aureus*—Derived Staphopain B, a Potent Cysteine Protease Activator of Plasma Chemerin", The Journal of Immunology, 178:3713-3720 (2007).
Roh et al., "Chemerin—A new adipokine that modulates adipogenesis via its own receptor", Biochemical and Biophysical Research Communications, 362:1013-1018 (2007).
Zabel et al., "Chemokine-like receptor 1 expression by macrophages in vivo: Regulation by TGF-B and TLR ligands", Experimental Hematology, 34:1106-1114 (2006).
Zabel et al., "Chemerin Activation by Serine Proteases of the Coagulation, Fibrinolytic, and Inflammatory Cascades", The Journal of Biological Chemistry, 280(41):34661-34666 (Oct. 14, 2005).
International Search Report and Written Opinion for PCT/GB2008/001020 dated Jul. 21, 2008.
Guillabert et al., "Role of neutrophil proteinase 3 and mast cell chymase in chemerin proteolytic regulation", Journal of Leukocyte Biology, 84:1-12 (Dec. 2008).

* cited by examiner

*Primary Examiner* — Bridget E Bunner
*Assistant Examiner* — Fozia Hamud
(74) *Attorney, Agent, or Firm* — Rodney J. Fuller; Booth Udall Fuller, PLC

(57) ABSTRACT

This invention provides the use of one or more peptides derived from the C-terminal end of a Chemerin protein, or analogs, or derivatives thereof for treatment of inflammation and/or endotoxic shock and/or treatment of wounds and/or reduction of levels of inflammatory chemokines in a subject, and one or more peptides derived from the C-terminal end of a Chemerin protein, or analogs or derivatives thereof for use in the treatment of inflammation and/or endotoxic shock, and/or wounds, or for the reduction or levels of inflammatory mediators.

22 Claims, 22 Drawing Sheets

SEQUENCE LISTING

<160> NUMBER OF SEQ ID NOS: 45

<210> SEQ ID NO 1
<211> LENGTH: 11
<212> TYPE: PRT
<213> ORGANISM: Mus sp.

<400> SEQUENCE: 1

Pro His Gly Tyr Phe Leu Pro Gly Gln Phe Ala
1               5                   10

<210> SEQ ID NO 2
<211> LENGTH: 12
<212> TYPE: PRT
<213> ORGANISM: Mus sp.

<400> SEQUENCE: 2

Pro His Gly Tyr Phe Leu Pro Gly Gln Phe Ala Phe
1               5                   10

<210> SEQ ID NO 3
<211> LENGTH: 13
<212> TYPE: PRT
<213> ORGANISM: Mus sp.

<400> SEQUENCE: 3

Pro His Gly Tyr Phe Leu Pro Gly Gln Phe Ala Phe Ser
1               5                   10

<210> SEQ ID NO 4
<211> LENGTH: 15
<212> TYPE: PRT
<213> ORGANISM: Mus sp.

<400> SEQUENCE: 4

Ala Gly Glu Asp Pro His Gly Tyr Phe Leu Pro Gly Gln Phe Ala
1               5                   10                  15

<210> SEQ ID NO 5
<211> LENGTH: 16
<212> TYPE: PRT
<213> ORGANISM: Mus sp.

<400> SEQUENCE: 5

Ala Gly Glu Asp Pro His Gly Tyr Phe Leu Pro Gly Gln Phe Ala Phe
1               5                   10                  15

<210> SEQ ID NO 6
<211> LENGTH: 17
<212> TYPE: PRT
<213> ORGANISM: Mus sp.

<400> SEQUENCE: 6

Ala Gly Glu Asp Pro His Gly Tyr Phe Leu Pro Gly Gln Phe Ala Phe
1               5                   10                  15

Ser

<210> SEQ ID NO 7
<211> LENGTH: 12
<212> TYPE: PRT
<213> ORGANISM: Mus sp.

<400> SEQUENCE: 7

Asp Pro His Gly Tyr Phe Leu Pro Gly Gln Phe Ala
1               5                   10

<210> SEQ ID NO 8
<211> LENGTH: 13
<212> TYPE: PRT
<213> ORGANISM: Mus sp.

<400> SEQUENCE: 8

Glu Asp Pro His Gly Tyr Phe Leu Pro Gly Gln Phe Ala
1               5                   10

<210> SEQ ID NO 9
<211> LENGTH: 14
<212> TYPE: PRT
<213> ORGANISM: Mus sp.

<400> SEQUENCE: 9

Gly Glu Asp Pro His Gly Tyr Phe Leu Pro Gly Gln Phe Ala
1               5                   10

<210> SEQ ID NO 10
<211> LENGTH: 13
<212> TYPE: PRT
<213> ORGANISM: Mus sp.

<400> SEQUENCE: 10

Asp Pro His Gly Tyr Phe Leu Pro Gly Gln Phe Ala Phe
1               5                   10

<210> SEQ ID NO 11
<211> LENGTH: 14
<212> TYPE: PRT
<213> ORGANISM: Mus sp.

<400> SEQUENCE: 11

Glu Asp Pro His Gly Tyr Phe Leu Pro Gly Gln Phe Ala Phe
1               5                   10

<210> SEQ ID NO 12
<211> LENGTH: 15
<212> TYPE: PRT
<213> ORGANISM: Mus sp.

<400> SEQUENCE: 12

Gly Glu Asp Pro His Gly Tyr Phe Leu Pro Gly Gln Phe Ala Phe
1               5                   10                  15

<210> SEQ ID NO 13
<211> LENGTH: 14
<212> TYPE: PRT
<213> ORGANISM: Mus sp.

<400> SEQUENCE: 13

Asp Pro His Gly Tyr Phe Leu Pro Gly Gln Phe Ala Phe Ser
1               5                   10

<210> SEQ ID NO 14
<211> LENGTH: 15
<212> TYPE: PRT
<213> ORGANISM: Mus sp.

<400> SEQUENCE: 14

Glu Asp Pro His Gly Tyr Phe Leu Pro Gly Gln Phe Ala Phe Ser
1               5                   10                  15

<210> SEQ ID NO 15
<211> LENGTH: 16
<212> TYPE: PRT
<213> ORGANISM: Mus sp.

<400> SEQUENCE: 15

Gly Glu Asp Pro His Gly Tyr Phe Leu Pro Gly Gln Phe Ala Phe Ser
1               5                   10                  15

<210> SEQ ID NO 16
<211> LENGTH: 11
<212> TYPE: PRT
<213> ORGANISM: Homo sapiens

<400> SEQUENCE: 16

Pro His Ser Phe Tyr Phe Pro Gly Gln Phe Ala
1               5                   10

<210> SEQ ID NO 17
<211> LENGTH: 12
<212> TYPE: PRT
<213> ORGANISM: Homo sapiens

<400> SEQUENCE: 17

Pro His Ser Phe Tyr Phe Pro Gly Gln Phe Ala Phe
1               5                   10

<210> SEQ ID NO 18
<211> LENGTH: 13
<212> TYPE: PRT
<213> ORGANISM: Homo sapiens

<400> SEQUENCE: 18

Pro His Ser Phe Tyr Phe Pro Gly Gln Phe Ala Phe Ser
1               5                   10

<210> SEQ ID NO 19
<211> LENGTH: 15
<212> TYPE: PRT
<213> ORGANISM: Homo sapiens

<400> SEQUENCE: 19

Ala Gly Glu Asp Pro His Ser Phe Tyr Phe Pro Gly Gln Phe Ala

```
                1               5                   10                  15
```

<210> SEQ ID NO 20
<211> LENGTH: 16
<212> TYPE: PRT
<213> ORGANISM: Homo sapiens

<400> SEQUENCE: 20

```
Ala Gly Glu Asp Pro His Ser Phe Tyr Phe Pro Gly Gln Phe Ala Phe
1               5                   10                  15
```

<210> SEQ ID NO 21
<211> LENGTH: 17
<212> TYPE: PRT
<213> ORGANISM: Homo sapiens

<400> SEQUENCE: 21

```
Ala Gly Glu Asp Pro His Ser Phe Tyr Phe Pro Gly Gln Phe Ala Phe
1               5                   10                  15

Ser
```

<210> SEQ ID NO 22
<211> LENGTH: 12
<212> TYPE: PRT
<213> ORGANISM: Homo sapiens

<400> SEQUENCE: 22

```
Asp Pro His Ser Phe Tyr Phe Pro Gly Gln Phe Ala
1               5                   10
```

<210> SEQ ID NO 23
<211> LENGTH: 13
<212> TYPE: PRT
<213> ORGANISM: Homo sapiens

<400> SEQUENCE: 23

```
Glu Asp Pro His Ser Phe Tyr Phe Pro Gly Gln Phe Ala
1               5                   10
```

<210> SEQ ID NO 24
<211> LENGTH: 14
<212> TYPE: PRT
<213> ORGANISM: Homo sapiens

<400> SEQUENCE: 24

```
Gly Glu Asp Pro His Ser Phe Tyr Phe Pro Gly Gln Phe Ala
1               5                   10
```

<210> SEQ ID NO 25
<211> LENGTH: 13
<212> TYPE: PRT
<213> ORGANISM: Homo sapiens

<400> SEQUENCE: 25

```
Asp Pro His Ser Phe Tyr Phe Pro Gly Gln Phe Ala Phe
1               5                   10
```

<210> SEQ ID NO 26
<211> LENGTH: 14
<212> TYPE: PRT
<213> ORGANISM: Homo sapiens

<400> SEQUENCE: 26

```
Glu Asp Pro His Ser Phe Tyr Phe Pro Gly Gln Phe Ala Phe
```

<210> SEQ ID NO 27
<211> LENGTH: 15
<212> TYPE: PRT
<213> ORGANISM: Homo sapiens

<400> SEQUENCE: 27

Gly Glu Asp Pro His Ser Phe Tyr Phe Pro Gly Gln Phe Ala Phe
1               5                   10                  15

<210> SEQ ID NO 28
<211> LENGTH: 14
<212> TYPE: PRT
<213> ORGANISM: Homo sapiens

<400> SEQUENCE: 28

Asp Pro His Ser Phe Tyr Phe Pro Gly Gln Phe Ala Phe Ser
1               5                   10

<210> SEQ ID NO 29
<211> LENGTH: 15
<212> TYPE: PRT
<213> ORGANISM: Homo sapiens

<400> SEQUENCE: 29

Glu Asp Pro His Ser Phe Tyr Phe Pro Gly Gln Phe Ala Phe Ser
1               5                   10                  15

<210> SEQ ID NO 30
<211> LENGTH: 16
<212> TYPE: PRT
<213> ORGANISM: Homo sapiens

<400> SEQUENCE: 30

Gly Glu Asp Pro His Ser Phe Tyr Phe Pro Gly Gln Phe Ala Phe Ser
1               5                   10                  15

<210> SEQ ID NO 31
<211> LENGTH: 137
<212> TYPE: PRT
<213> ORGANISM: Homo sapiens

<400> SEQUENCE: 31

Glu Leu Thr Glu Ala Gln Arg Arg Gly Leu Gln Val Ala Leu Glu Glu
1               5                   10                  15

Phe His Lys His Pro Pro Val Gln Trp Ala Phe Gln Glu Thr Ser Val
                20                  25                  30

Glu Ser Ala Val Asp Thr Pro Phe Pro Ala Gly Ile Phe Val Arg Leu
            35                  40                  45

Glu Phe Lys Leu Gln Gln Thr Ser Cys Arg Lys Arg Asp Trp Lys Lys
        50                  55                  60

Pro Glu Cys Lys Val Arg Pro Asn Gly Lys Arg Lys Cys Leu Ala
65                  70                  75                  80

Cys Ile Lys Leu Gly Ser Glu Asp Lys Val Leu Gly Arg Leu Val His
                85                  90                  95

Cys Pro Ile Glu Thr Gln Val Leu Arg Glu Ala Glu His Gln Glu
                100                 105                 110

Thr Gln Cys Leu Arg Val Gln Arg Ala Gly Glu Asp Pro His Ser Phe
            115                 120                 125

Tyr Phe Pro Gly Gln Phe Ala Phe Ser

```
            130                 135

<210> SEQ ID NO 32
<211> LENGTH: 143
<212> TYPE: PRT
<213> ORGANISM: Homo sapiens

<400> SEQUENCE: 32

Glu Leu Thr Glu Ala Gln Arg Arg Gly Leu Gln Val Ala Leu Glu Glu
1               5                   10                  15

Phe His Lys His Pro Pro Val Gln Trp Ala Phe Gln Glu Thr Ser Val
            20                  25                  30

Glu Ser Ala Val Asp Thr Pro Phe Pro Ala Gly Ile Phe Val Arg Leu
        35                  40                  45

Glu Phe Lys Leu Gln Gln Thr Ser Cys Arg Lys Arg Asp Trp Lys Lys
    50                  55                  60

Pro Glu Cys Lys Val Arg Pro Asn Gly Arg Lys Arg Lys Cys Leu Ala
65                  70                  75                  80

Cys Ile Lys Leu Gly Ser Glu Asp Lys Val Leu Gly Arg Leu Val His
                85                  90                  95

Cys Pro Ile Glu Thr Gln Val Leu Arg Glu Ala Glu Glu His Gln Glu
            100                 105                 110

Thr Gln Cys Leu Arg Val Gln Arg Ala Gly Glu Asp Pro His Ser Phe
        115                 120                 125

Tyr Phe Pro Gly Gln Phe Ala Phe Ser Lys Ala Leu Pro Arg Ser
    130                 135                 140

<210> SEQ ID NO 33
<211> LENGTH: 163
<212> TYPE: PRT
<213> ORGANISM: Homo sapiens

<400> SEQUENCE: 33

Met Arg Arg Leu Leu Ile Pro Leu Ala Leu Trp Leu Gly Ala Val Gly
1               5                   10                  15

Val Gly Val Ala Glu Leu Thr Glu Ala Gln Arg Arg Gly Leu Gln Val
            20                  25                  30

Ala Leu Glu Glu Phe His Lys His Pro Pro Val Gln Trp Ala Phe Gln
        35                  40                  45

Glu Thr Ser Val Glu Ser Ala Val Asp Thr Pro Phe Pro Ala Gly Ile
    50                  55                  60

Phe Val Arg Leu Glu Phe Lys Leu Gln Gln Thr Ser Cys Arg Lys Arg
65                  70                  75                  80

Asp Trp Lys Lys Pro Glu Cys Lys Val Arg Pro Asn Gly Arg Lys Arg
                85                  90                  95

Lys Cys Leu Ala Cys Ile Lys Leu Gly Ser Glu Asp Lys Val Leu Gly
            100                 105                 110

Arg Leu Val His Cys Pro Ile Glu Thr Gln Val Leu Arg Glu Ala Glu
        115                 120                 125

Glu His Gln Glu Thr Gln Cys Leu Arg Val Gln Arg Ala Gly Glu Asp
    130                 135                 140

Pro His Ser Phe Tyr Phe Pro Gly Gln Phe Ala Phe Ser Lys Ala Leu
145                 150                 155                 160

Pro Arg Ser

<210> SEQ ID NO 34
```

```
<211> LENGTH: 140
<212> TYPE: PRT
<213> ORGANISM: Mus sp.

<400> SEQUENCE: 34

Thr Val Gly Thr Glu Pro Glu Leu Ser Glu Thr Gln Arg Arg Ser Leu
1               5                   10                  15

Gln Val Ala Leu Glu Glu Phe His Lys His Pro Val Gln Leu Ala
            20                  25                  30

Phe Gln Glu Ile Gly Val Asp Arg Ala Glu Glu Val Leu Phe Ser Ala
                35                  40                  45

Gly Thr Phe Val Arg Leu Glu Phe Lys Leu Gln Gln Thr Asn Cys Pro
        50                  55                  60

Lys Lys Asp Trp Lys Lys Pro Glu Cys Thr Ile Lys Pro Asn Gly Arg
65                  70                  75                  80

Arg Arg Lys Cys Leu Ala Cys Ile Lys Met Asp Pro Lys Gly Lys Ile
                85                  90                  95

Leu Gly Arg Ile Val His Cys Pro Ile Leu Lys Gln Gly Pro Gln Asp
                100                 105                 110

Pro Gln Glu Leu Gln Cys Ile Lys Ile Ala Gln Ala Gly Glu Asp Pro
            115                 120                 125

His Gly Tyr Phe Leu Pro Gly Gln Phe Ala Phe Ser
        130                 135                 140

<210> SEQ ID NO 35
<211> LENGTH: 146
<212> TYPE: PRT
<213> ORGANISM: Mus sp.

<400> SEQUENCE: 35

Thr Val Gly Thr Glu Pro Glu Leu Ser Glu Thr Gln Arg Arg Ser Leu
1               5                   10                  15

Gln Val Ala Leu Glu Glu Phe His Lys His Pro Val Gln Leu Ala
            20                  25                  30

Phe Gln Glu Ile Gly Val Asp Arg Ala Glu Glu Val Leu Phe Ser Ala
                35                  40                  45

Gly Thr Phe Val Arg Leu Glu Phe Lys Leu Gln Gln Thr Asn Cys Pro
        50                  55                  60

Lys Lys Asp Trp Lys Lys Pro Glu Cys Thr Ile Lys Pro Asn Gly Arg
65                  70                  75                  80

Arg Arg Lys Cys Leu Ala Cys Ile Lys Met Asp Pro Lys Gly Lys Ile
                85                  90                  95

Leu Gly Arg Ile Val His Cys Pro Ile Leu Lys Gln Gly Pro Gln Asp
                100                 105                 110

Pro Gln Glu Leu Gln Cys Ile Lys Ile Ala Gln Ala Gly Glu Asp Pro
            115                 120                 125

His Gly Tyr Phe Leu Pro Gly Gln Phe Ala Phe Ser Arg Ala Leu Arg
        130                 135                 140

Thr Lys
145

<210> SEQ ID NO 36
<211> LENGTH: 162
<212> TYPE: PRT
<213> ORGANISM: Mus sp.

<400> SEQUENCE: 36
```

```
Met Lys Cys Leu Leu Ile Ser Leu Ala Leu Trp Leu Gly Thr Arg Gly
1               5                   10                  15

Thr Val Gly Thr Glu Pro Glu Leu Ser Glu Thr Gln Arg Arg Ser Leu
            20                  25                  30

Gln Val Ala Leu Glu Glu Phe His Lys His Pro Pro Val Gln Leu Ala
        35                  40                  45

Phe Gln Glu Ile Gly Val Asp Arg Ala Glu Val Leu Phe Ser Ala
    50                  55                  60

Gly Thr Phe Val Arg Leu Glu Phe Lys Leu Gln Gln Thr Asn Cys Pro
65                  70                  75                  80

Lys Lys Asp Trp Lys Lys Pro Glu Cys Thr Ile Lys Pro Asn Gly Arg
                85                  90                  95

Arg Arg Lys Cys Leu Ala Cys Ile Lys Met Asp Pro Lys Gly Lys Ile
            100                 105                 110

Leu Gly Arg Ile Val His Cys Pro Ile Leu Lys Gln Gly Pro Gln Asp
            115                 120                 125

Pro Gln Glu Leu Gln Cys Ile Lys Ile Ala Gln Ala Gly Glu Asp Pro
    130                 135                 140

His Gly Tyr Phe Leu Pro Gly Gln Phe Ala Phe Ser Arg Ala Leu Arg
145                 150                 155                 160

Thr Lys

<210> SEQ ID NO 37
<211> LENGTH: 19
<212> TYPE: PRT
<213> ORGANISM: Mus sp.

<400> SEQUENCE: 37

Ala Gln Ala Gly Glu Asp Pro His Gly Tyr Phe Leu Pro Gly Gln Phe
1               5                   10                  15

Ala Phe Ser

<210> SEQ ID NO 38
<211> LENGTH: 19
<212> TYPE: PRT
<213> ORGANISM: Homo sapiens

<400> SEQUENCE: 38

Gln Arg Ala Gly Glu Asp Pro His Ser Phe Tyr Phe Pro Gly Gln Phe
1               5                   10                  15

Ala Phe Ser

<210> SEQ ID NO 39
<211> LENGTH: 15
<212> TYPE: PRT
<213> ORGANISM: Artificial Sequence
<220> FEATURE:
<223> OTHER INFORMATION: Scrambled C15

<400> SEQUENCE: 39

Gly Leu Phe His Asp Gln Ala Gly Pro Pro Ala Gly Tyr Glu Phe
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Mutant C15
```

```
<400> SEQUENCE: 40

Ala Gly Glu Asp Pro His Gly Tyr Ala Leu Pro Gly Gln Ala Ala
1               5                   10                  15

<210> SEQ ID NO 41
<211> LENGTH: 6
<212> TYPE: PRT
<213> ORGANISM: Mus sp.

<400> SEQUENCE: 41

Arg Ala Leu Arg Thr Lys
1               5

<210> SEQ ID NO 42
<211> LENGTH: 8
<212> TYPE: PRT
<213> ORGANISM: Mus sp.

<400> SEQUENCE: 42

Phe Ser Arg Ala Leu Arg Thr Lys
1               5

<210> SEQ ID NO 43
<211> LENGTH: 13
<212> TYPE: PRT
<213> ORGANISM: Artificial Sequence
<220> FEATURE:
<223> OTHER INFORMATION: Modified C13h

<400> SEQUENCE: 43

Phe His Ser Phe Tyr Phe Pro Gly Gln Phe Ala Phe Ser
1               5                   10

<210> SEQ ID NO 44
<211> LENGTH: 19
<212> TYPE: PRT
<213> ORGANISM: Mus sp.

<400> SEQUENCE: 44

Glu Leu Ser Glu Thr Gln Arg Arg Ser Leu Gln Val Ala Leu Glu Glu
1               5                   10                  15

Phe His Lys

<210> SEQ ID NO 45
<211> LENGTH: 20
<212> TYPE: PRT
<213> ORGANISM: Mus sp.

<400> SEQUENCE: 45

Lys Pro Glu Cys Thr Ile Lys Pro Asn Gly Arg Arg Lys Cys Leu
1               5                   10                  15

Ala Cys Ile Lys
            20
```

TREATMENT OF INFLAMMATION AND/OR ENDOTOXIC SHOCK

This application is the U.S. national stage of PCT/GB2008/001020 filed Mar. 25, 2008, which claims priority to and benefit of Great Britain Patent Application No. 0705488.5 filed Mar. 22, 2007, the contents of each of which are herein incorporated by reference for all purposes.

FIELD OF THE INVENTION

This invention relates to the treatment of inflammation and/or endotoxic shock and/or to the reduction of levels of inflammatory chemokines, and to compositions for use in the treatment of inflammation and/or endotoxic shock, or for the reduction of levels of inflammatory mediators.

BACKGROUND

Inflammation is a component of the pathogenesis of many human and animal diseases, as well as arising as a result of physical, chemical or traumatic damage to tissues in a human or animal body. In general, the immune response results in the systemic release of endogenous chemical mediators which cause vasodilation, migration of neutrophils, chemotaxis, and increased vascular permeability. The immune response is essentially the same wherever it occurs and whatever the cause. The response can be acute (short lived) or it may be chronic (long lasting).

Endotoxic shock, sometimes also referred to as septic shock, is thought to occur due to intravascular exposure to large amounts of endotoxin resulting in an inflammation like response. Exposure to endotoxin results in the production of a number of cytokines, including TNFα and IL-1. The complement system and the coagulation cascade, including Factor VII are also stimulated. The result of this reaction can be tissue damage, fever, vasodilation, tachycardia and intravascular coagulation.

An inflammatory response is typically beneficial, giving the site of inflammation increased access to nutrients, oxygen, antibodies and therapeutic drugs, as well as increased fibrin formation and dilution of toxins. However, if inflammation is unwanted or prolonged then it can cause damage to the tissue. In such situations, anti-inflammatory drugs are often used. There are two main types of anti-inflammatory drugs, corticosteroids and non-steroidal anti-inflammatory drugs (NSAIDs).

Most of these drugs have unwanted side effects. Prolonged corticosteroid administration is frequently associated with serious side effects that mimic Cushing's disease, a malfunction of the adrenal glands resulting in overproduction of cortisol. Other potential side effects include weight gain, fat deposits in the chest, face, neck and upper back, oedema, hypertension, diabetes, poor wound healing, increased susceptibility to infection, thinning of the skin, mood swings and depression. The most serious side effects of NSAIDS are kidney failure, liver failure, ulcers and prolonged bleeding after an injury or surgery. Some individuals are allergic to NSAIDs and people with asthma are at a higher risk for experiencing a serious allergic reaction to aspirin. There is therefore a need to identify alternative agents which have anti-inflammatory effects.

Chemerin is an abundant protein present in a range of human inflammatory exudates including ascitic and synovial fluid (Wittamer V et al. J Exp Med. Oct. 6, 2003; 198(7):977-985; Meder W et al. FEBS Lett. Dec. 18, 2003; 555(3):495-499). Human Chemerin is secreted as a 163 amino acid (aa) precursor referred to as ProChemerin (the *Mus musculus*, murine equivalent is 162aa) which undergoes N- and C-terminal truncation to generate a 137aa chemotactic protein (140aa in *Mus musculus*) (Wittamer V et al. J Exp Med. Oct. 6, 2003; 198(7):977-985; Zabel B A et al. J Biol Chem. Oct. 14, 2005; 280(41):34661-34666; Wittamer V et al. J Immunol. Jul. 1, 2005; 175(1):487-493; Samson M et al. Eur J Immunol. May 1998; 28(5):1689-1700). The predicted structure for Chemerin indicates structural similarities to chemokines and it has been described as a "reverse" chemokine, potentially possessing a disordered carboxyl-terminus, an α-pleated sheet and a β-helical amino-terminal domain (Zabel B A et al. Exp Hematol. August 2006; 34(8):1021-1032). The structure is reminiscent of the cystatin fold present in cathelicidins and kininogens which also undergo proteolytic processing to achieve activation (Zabel B A et al. Exp Hematol. August 2006; 34(8):1106-1114; Colman R W, Biol Chem. January 2001; 382(1):65-70; Yamasaki K et al. FASEB J. Oct. 1, 2006 2006; 20(12):2068-2080).

SUMMARY

According to a first aspect, the present invention provides the use of one or more peptides derived from the C-terminal end of a Chemerin protein, or analogs or derivatives thereof, in the preparation of a medicament for the treatment of inflammation.

According to another aspect, the invention provides the use of one or more peptides derived from the C-terminal end of a Chemerin protein, or analogs or derivatives thereof, in the preparation of a medicament for the treatment of endotoxic shock.

According to a further aspect, the invention provides the use of one or more peptides derived from the C-terminal end of a Chemerin protein, or analogs or derivatives thereof, in the preparation of a medicament for reducing the level of one or more inflammatory mediators.

According to a yet further aspect, the present invention provides one or more peptides derived from the C-terminal end of a Chemerin protein, or analogs or derivatives thereof, for use in the treatment of inflammation, and/or in the treatment of endotoxic shock, and/or to reduce the level of one or more inflammatory mediators.

The one or more inflammatory mediators may include cytokines, chemokines and lipids that mediate inflammation. The inflammatory mediator may include one or more chemokines selected from the group comprising TNFα, IL-1α, IL-1β, IL-6, IL-12, G-CSF, MCP-2 (CCL8), GROα (CXCL1), GROβ (CXCL2), IL-8 (CXCL8), TECK (CCL25), MCP-1 (CCL2), interferon γ and RANTES (CCL5). Preferably, the medicament can reduce levels of TNFα.

Surprisingly, peptides derived from the C-terminal end of the Chemerin protein have anti-inflammatory properties, and may be used to treat, prevent or ameliorate inflammation and/or endotoxic shock.

The medicament may have a therapeutic and/or a prophylactic use.

Preferably, the peptide is between about 5 and about 30 amino acids. More preferably, the peptide is between about 5 and about 25 amino acids, preferably, the peptide is between about 5 and about 20 amino acids.

Preferably the peptide comprises between about 5 and about 30 amino acids derived from the C-terminal end of a Chemerin protein, or an analog or a derivative thereof. More preferably, the peptide is between about 5 and about 25 amino acids, preferably, the peptide is between about 5 and about 20 amino acids.

Reference to a Chemerin protein means the processed form of Chemerin, in which the N-terminal amino acids found in the PreProChemerin have been proteolytically removed, and the C-terminal amino acids found in ProChemerin precursor have been proteolytically removed to produce the active truncated form of the protein referred to as Chemerin.

Preferably the peptide is derived from a human or non-human form of Chemerin. Preferably the peptide is derived from a human or mammalian form of Chemerin. The mammalian non-human Chemerin may be derived from a rodent, such as a rat or a mouse, a horse, a dog, a cat, a cow, a sheep or a pig.

Preferably the peptide derived from the C-terminal end of a Chemerin protein has at least 30% or higher identity with the naturally occurring C-terminal end of the Chemerin protein. Preferably the peptide has at least 40%, 50%, 60%, 70%, 80%, 90% or higher identity with the naturally occurring peptide sequence at the C-terminal end of the Chemerin protein.

Preferably the peptide has at least 30% or higher sequence identity with between about the last 5 and about the last 30, preferably between about the last 10 and about the last 25, amino acids which naturally occur at the C-terminal end of a Chemerin protein. Preferably the peptide has at least about 40%, 50%, 60%, 70%, 80%, 90% or higher sequence identity with between about the last 5 and about the last 30, preferably between about the last 10 and about the last 25, amino acids which naturally occur at the C-terminal end of a Chemerin protein.

Preferably the peptide has at least 30% or higher sequence identity with between 5 and 25 amino acids in the last 30 amino acids which naturally occur at the C-terminal end of a Chemerin protein. Preferably the peptide has at least about 40%, 50%, 60%, 70%, 80%, 90% or higher sequence identity with between 5 and 25 amino acids in the last 30 amino acids which naturally occur at the C-terminal end of a Chemerin protein.

Reference to the "last amino acids" in the Chemerin protein refers to the amino acids at the C-terminal end of the protein.

The full-length sequence of human and murine Chemerin, ProChemerin and PreProChemerin is given in FIG. 2A, and reflected in Seq ID nos: 31, 32, 33, respectively for the human proteins, and Seq ID nos: 34, 35, 36, respectively for the mouse proteins. Preferably the Chemerin peptide has the sequence of Seq ID No: 31 or 34. The sequence of Chemerin proteins from other species, such as bovine and rat, are readily available from GenBank and can be easily accessed by those skilled in the art.

Preferably the peptide has at least 30% or higher, more preferably 40%, 50%, 60%, 70%, 80%, 90% or higher sequence identity with between the last 5 and the last 30 amino acids of the Chemerin according to Seq ID no: 31 (human sequence) and Seq ID no: 34 (mouse sequence).

Percentage amino acid sequence identity is defined as the percentage of amino acid residues in a sequence that is identical with the amino acids in the naturally occurring Chemerin protein after aligning the sequences and introducing gaps if necessary to achieve the maximum percent sequence identity. Alignment for purpose of determining percent sequence identify can be achieved in many ways that are well known to the man skilled in the art, and include, for example, using BLAST and ALIGN algorithms.

The peptide may contain additions, insertions, deletions, inversions or translocations relative to the natural sequence of the C-terminal end of a Chemerin protein, provided that the peptide has at least 50% of the anti-inflammatory activity of, and/or at least 50% of the anti-endotoxic shock activity of, and/or the ability to reduce the level of one or more inflammatory mediators by at least 50% compared to, a peptide having the natural sequence.

The terms "analog" or "derivative" refers to peptides which have a sequence different to the naturally occurring sequence but which comprises essentially the same or more, and at least about 50%, preferably about 60%, 70%, 80% or 90%, of the anti-inflammatory activity, and/or the anti-endotoxic shock activity, inflammatory mediator reducing activity, observed with a peptide having a naturally occurring sequence.

A peptide analog or derivative may have one or more deletion, insertion, or modification of any amino acid residue, including the N or C-terminal residue. The peptide may be acetylated, acylated, alkylated, glycosylated, and the like. The peptide may also comprise additional amino acids either at the C or N terminal end, or at both ends.

The peptide, analog or derivative may be part of a fusion protein.

The peptide may include one or more conservative amino acid substitutions as compared with the naturally occurring amino acid sequence.

Preferably one or more of the peptides comprises a sequence selected from the group comprising:

```
PHGYFLPGQPA;
(Chemerin11-mouse; Chin; Seq ID No: 1)

PHGYFLPGQFAF;
(Chemerin12-mouse; C12m; Seq ID No: 2)

PHGYFLPGQFAFS;
(Chemerin13-mouse; C13m; Seq ID No: 3)

AGEDPHGYFLPGQFA;
(Chemerin15-mouse; C15m; Seq ID No: 4)

AGEDPHGYFLPGQFAF;
(Chemerin16-mouse; C16m; Seq ID No: 5)

AGEDPHGYFLPGQFAFS;
(Chemerin17-mouse; C17m; Seq ID No: 6)

DPHGYFLPGQFA;
(Chemerin12A-mouse; C12Am; Seq ID No: 7)

EDPHGYFLPGQFA;
(Chemerin13A-mouse; C13Am; Seq ID No: 8)

GEDPHGYPLPGQFA;
(Chemerin14A-mouse; C14Am; Seq ID No: 9)

DPHGYFLPGQFAF;
(Chemerin13B-mouse; C13Bm; Seq ID No: 10)

EDPHGYFLPGQFAF;

(Chemerin14B-mouse; C14Bm; Seq ID No: 11)

GEDPHGYFLPGQFAF;
(Chemerin15A-mouse; C15Am; Seq ID No: 12)

DPHGYFLPGQFAFS;
(Chemerin14C-mouse; C14Cm; Seq ID No: 13)

EDPHGYFLPGQFAFS;
(Chemerin15B-mouse; C15Bm; Seq ID No: 14)

GEDPHGYFLPGQFAFS;
(Chemerin16A-mouse; C16Am; Seq ID No: 15)
```

-continued

```
PHSEYFPGQFA;
(Chemerin11-human; C11h; Seq ID No: 16)

PHSFYFPGQFAF;
(Chemerin12-human; C12h; Seq ID No:17)

PHSFYFPGQFAFS;
(Chemerin13-human; C13h; Seq ID No: 18)

AGEDPHSFYFPGQFA;
(Chemerin15-human; C15h; Seq ID No: 19)

AGEDPHSFYPPGQFAF;
(Chemerin16-human; C16h; Seq ID No: 20)

AGEDPHSFYFPGQFAFS;
(Chemerin17-human; C17h; Seq ID No: 21)

DPHSFYFPGQFA;
(Chemerin12A-human; C12Ah; Seq ID No: 22)

EDPHSFYFPGQFA;
(Chemerin13k-human; C13Ah; Seq ID No: 23)

GEDPHSPYFPGQFA;
(Chemerin14A-human; C14Ah; Seq ID No: 24)

DPHSFYPPGQFAF;
(Chemerin13B-human; C13Bh; Seq ID No: 25)

EDPHSFYFPGQFAF;
(Chemerin14B-human; C14Bh; Seq ID No: 26)

GEDPHSFYFPGQFAF;
(Chemerin15A-human; C15Ah; Seq ID No: 27)

DPHSFYFPGQFAPS;
(Chemerin14C-human; C14Ch; Seq ID No: 28)

EDPHSFYFPGQFAFS;
(Chemerin15B-human; C15Bh; Seq ID No: 29)
and

GEDPHSFYFPGQFAFS;
(Chemerin16A-human; C16Ah; Seq ID No: 30)
``` or analogs or derivatives thereof.

Preferably one or more of the peptides comprises a sequence selected from the group comprising:
AQAGEDPHGYFLPGQFAFS (Chemerin19-mouse; C19m; Seq ID No: 37); and
QRAGEDPHSFYFPGQFAFS (Chemerin19-human; C19h; Seq ID No: 38); or analogs or derivatives thereof.

Preferably the peptide has at least 30%, 40%, 50%, 60%, 70%, 80%, 90% or higher sequence identity with one or more of the peptides referred to above as Seq ID No: 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30.

Preferably the peptide has at least 30%, 40%, 50%, 60%, 70%, 80%, 90% or higher sequence identity with one or more of the peptides referred to above as Seq ID No: 37 or 38.

Preferably an analog or derivative of a peptide derived from the C-terminal end of a Chemerin protein includes small molecule mimetics of a peptide.

The peptide, analog or derivative, may be isolated from a natural system, or it may be synthetically or recombinantly produced. Synthesised peptides may be produced by standard chemical methods, including synthesis by automated procedure.

Recombinant peptides may be used in a purified form. Alternatively, the supernatant from cells expressing the recombinant peptide may be used.

The peptide, analog or derivative may form part of a larger protein or molecular complex.

The peptide may be a straight chain or cyclic.

The peptide may include a protease resistant backbone.

The peptide may include modifications at the C and/or N terminus.

The peptide may be labelled, such as with a radioactive label, fluorescent label, a mass spectrometry tag, biotin or the like, by methods known in the art.

The medicament may comprise other active ingredients, including other known anti-inflammatory agents, and/or other known anti-endotoxic shock agents, and/or other agents known to reduce chemokines levels.

The medicament may also contain a pharmaceutically acceptable excipient. The excipient may comprise large macromolecules such as proteins, polysaccharides, polylactic acids, polyglycolic acids, polymeric amino acids, amino acid copolymers, trehalose, lipid aggregates and inactive virus particles. Such excipients will be well known to those skilled in the art.

The medicament may also comprise one or more of a buffering agent, a viscosity-increasing agent, a solvent, a stabiliser and a preservative.

The route of administration of the medicament may be injection or infusion by parenteral, subcutaneous, intravenous, intramuscular, intraperitoneal, intraarterial, intralesional, intrarticular, topical, oral, rectal, nasal, inhalation or any other suitable route.

The dosage of the peptides used will depend on the peptide, the target and the treatment. The determination of the dosage and route of administration is well within the skill of an ordinary physician. Normal dosage regimes may vary from about 1 pg/kg to about 100 mg/kg, more preferably the dosage will be from about 10 pg/kg to about 1 mg/kg, more preferably from about 10 pg/kg to about 100 ng/kg. Preferably these dosages are doses per day.

Surprisingly it has been found that a dose as low as 0.32 ng/kg of a peptide according to the invention has efficacy against sterile peritonitis in mice, whereas 1.2 mg/kg of dexamethasone is required to observe a similar degree of efficacy.

Preferably a medicament according to a use of the invention may be intended for administration at a dose of between about 10 pg/kg and about 1 mg/kg, more preferably at a dose of between about 10 pg/kg and about 100 ng/kg, or between about 10 pg/kg and about 10 ng/kg. These doses are at least three logs lower than the dose of dexamethasone needed.

According to another aspect the invention provides a method of treating, preventing or ameliorating inflammation in a subject comprising administering to the subject one or more peptides derived from the C-terminal end of a Chemerin protein, or analogs or derivatives thereof.

According to another aspect the invention provides a method of treating, preventing or ameliorating endotoxic shock in a subject comprising administering to the subject one or more peptides derived from the C-terminal end of a Chemerin protein, or analogs or derivatives thereof.

According to another aspect the invention provides a method of reducing the level of one or more inflammatory mediators in a subject comprising administering to the subject one or more peptides derived from the C-terminal end of a Chemerin protein, or analogs or derivatives thereof.

The treatment may be therapeutic, prophylactic or cosmetic.

Preferably the peptide is administered in an effective amount, that is, in an amount sufficient to: (i) induce or cause a reduction in inflammation, or which prevents or reduces inflammation; (ii) induce or cause a reduction in endotoxic shock, or which prevents or reduces endotoxic shock; and/or (iii) reduce the level of one or more inflammatory mediators.

Alternatively the medicament of the invention may be applied directly to a medical device to reduce the risk of device related inflammation. This may be achieved by applying the medicament to the surface of the device or by impregnating the surface of the device with one or more peptides derived from the C-terminal end of a Chemerin protein, or analogs or derivatives thereof.

According to another aspect, the invention provides a medical device impregnated with one or more peptides derived from the C-terminal end of a Chemerin protein, or analogs or derivatives thereof.

The medical device may be a stent or a catheter.

According to another aspect, the invention provides a wound dressing or bandage impregnated with one or more peptides derived from the C-terminal end of a Chemerin protein, or analogs or derivatives thereof.

The inflammation referred to in any aspect of the invention may be associated with a condition such as juvenile chronic arthritis, spondyloarthropathies, systemic sclerosis (scleroderma), idiopathic inflammatory myopathies (dermatomyositis, polymyositis), Sjogren's syndrome, systemic vasculitis, sarcoidosis, autoimmune hemolytic anemia (immune pancytopenia, paroxysmal nocturnal hemoglobinuria), autoimmune thrombocytopenia (idiopathic thrombocytopenic purpura, immunemediated thrombocytopenia), thyroiditis (Grave's disease, Hashimoto's thyroiditis, juvenile lymphocytic thyroiditis, atrophic thyroiditis), autoimmune inflammatory diseases (e.g., allergic encephalomyelitis, multiple sclerosis, insulin-dependent diabetes mellitus, autoimmune uveoretinitis, thyrotoxicosis, scleroderma, systemic lupus erythematosus, rheumatoid arthritis, inflammatory bowel disease (e.g., Crohn's disease, ulcerative colitis, regional enteritis, distal ileitis, granulomatous enteritis, regional ileitis, terminal ileitis), autoimmune thyroid disease, pernicious anemia, allograft rejection, diabetes mellitus, immune-mediated renal disease (glomerulonephritis, tubulointerstitial nephritis), demyelinating diseases of the central and peripheral nervous systems such as multiple sclerosis, idiopathic demyelinating polyneuropathy or Guillain-Barre syndrome, and chronic inflammatory demyelinating polyneuropathy, hepatobiliary diseases such as infectious hepatitis (hepatitis A, B, C, D, E and other non-hepatotropic viruses), autoimmune chronic active hepatitis, primary biliary cirrhosis, granulomatous hepatitis, sclerosing cholangitis, gluten-sensitive enteropathy, Whipple's disease, autoimmune or immune-mediated skin diseases including bullous skin diseases, erythema multiforme and contact dermatitis, psoriasis, allergic diseases such as asthma, allergic rhinitis, atopic dermatitis, food hypersensitivity and urticaria, immunologic diseases of the lung such as eosinophilic pneumonias, idiopathic pulmonary fibrosis and hypersensitivity pneumonitis, transplantation associated diseases including graft rejection and graftversus-host-disease, infectious diseases including viral diseases such as AIDS(HIV infection), herpes, etc., bacterial infections, fungal infections, protozoal infections, parasitic infections, and respiratory syncytial virus, human immunodeficiency virus, etc., eczema and endotoxic shock.

According to a further aspect the invention provides a peptide capable of treating, preventing or ameliorating inflammation selected from the group comprising peptides with the sequence of Seq ID No: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 and analogs or derivatives thereof.

According to a further aspect the invention provides a peptide capable of treating, preventing or ameliorating inflammation selected from the group comprising peptides with the sequence of Seq ID No: 37, 38 and analogs or derivatives thereof.

According to a further aspect the invention provides a peptide capable of treating, preventing or ameliorating endotoxic shock selected from the group comprising peptides with the sequence of Seq ID No: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 and analogs or derivatives thereof.

According to a further aspect the invention provides a peptide capable of treating, preventing or ameliorating endotoxic shock selected from the group comprising peptides with the sequence of Seq ID No: 37, 38 and analogs or derivatives thereof.

According to a further aspect the invention provides a peptide capable of reducing the level of one or more inflammatory mediators selected from the group comprising peptides with the sequence of Seq ID No: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 and analogs or derivatives thereof.

According to a further aspect the invention provides a peptide capable of reducing the level of one or more inflammatory mediators selected from the group comprising peptides with the sequence of Seq ID No: 37, 38 and analogs or derivatives thereof.

According to another aspect the invention provides a pharmaceutical composition comprising one or more peptides selected from the group comprising peptides with the sequence of Seq ID No: 1, 2, 3, 4, 5, 6, 7, 8, 9, 10, 11, 12, 13, 14, 15, 16, 17, 18, 19, 20, 21, 22, 23, 24, 25, 26, 27, 28, 29 and 30 and analogs or derivatives thereof.

According to another aspect the invention provides a pharmaceutical composition comprising one or more peptides selected from the group comprising peptides with the sequence of Seq ID No: 37 and 38 and analogs or derivatives thereof.

The pharmaceutical composition may be for the treatment and/or prevention of inflammation, and/or the treatment and/or prevention of endotoxic shock, and/or for the reduction of the level of one or more inflammatory mediators, such as cytokines and chemokines.

According to a further aspect the invention provides a peptide having the sequence of Seq ID No: 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 or an analog or derivative thereof.

According to a further aspect the invention provides a peptide having the sequence of Seq ID No: 37 or 38 or an analog or derivative thereof.

According to a further aspect the invention provides a peptide having at least 50% sequence identity to a peptide having the sequence of Seq ID No: 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30. Preferably the peptide has at least 60%, 70%, 80%, 90% or 95% sequence identity to a peptide having the sequence of Seq ID No: 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30.

According to a further aspect the invention provides a peptide having at least 50% sequence identity to a peptide having the sequence of Seq ID No: 37 or 38. Preferably the peptide has at least 60%, 70%, 80%, 90% or 95% sequence identity to a peptide having the sequence of Seq ID No: 37 or 38.

According to a further aspect the invention provides use of one or more peptides derived from the C-terminal end of a Chemerin protein, or analogs or derivatives thereof, in the preparation of a medicament for the treatment of a wound.

According to a further aspect the invention provides a method of treating, preventing or ameliorating a wound in a subject comprising administering to the subject one or more peptides derived from the C-terminal end of a Chemerin protein, or analogs or derivatives thereof.

According to a further aspect the invention provides a pharmaceutical composition comprising one or more peptides selected from the group comprising peptides with the sequence of Seq ID No: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 37 or 38 or an analog or derivative thereof for the treatment of a wound.

According to a further aspect the invention provides one or more peptides derived from the C-terminal end of a Chemerin protein, or analogs or derivatives thereof, for use in the treatment and/or prevention of inflammation, and/or the treatment and/or prevention of endotoxic shock, and/or for the reduction of the level of one or more inflammatory mediators, such as cytokines and chemokines.

According to a further aspect the invention provides one or more peptides derived from the C-terminal end of a Chemerin protein, or analogs or derivatives thereof, for use in the treatment of a wound.

The skilled man will appreciate that any of the preferable features discussed above can be applied to any of the aspects of the invention.

Preferred embodiments of the present invention will now be described, merely by way of example, with reference to the following figures and examples.

BRIEF DESCRIPTION OF THE DRAWINGS

FIG. 1C—Macrophage cytokine mRNA levels were quantitated by qRT-PCR (IL-10, TGFβ) and normalized to HPRT. FIG. 1D—PMΦ were pre-treated with chemerin (0.1-1 pM)±pertussis toxin (PTX; 200 ng/ml) prior to LPS/IFNγ-challenge. FIG. 1E—PMΦ were pre-treated with chemerin (1 pM) for 1 h±PTX and then stimulated with LPS/IFNγ for 4 h, 8 h or 15 h. *, p<0.001; , p<0.01; *, p<0.05 relative to LPS/IFNγ-treated samples. ###, p<0.001; ##, p<0.01; #, p<0.05 relative to chemerin-treated samples. FIG. 1F—peritoneal macrophages (PMΦ) were pre-treated with chemerin (1 pM), chemerin (1 pM)+protease inhibitor (Leupeptin [Leu], E-64, Pefabloc [Pef], Pepstatin A [Pep A], Calpeptin [Cal], Cathepsin S inhibitor [Cath S], Cathepsin L inhibitor [Cath L]) for 1 h and then stimulated with LPS (100 ng/ml) and IFNγ (20 ng/ml) for 15 h. Graphs show mean values±SEM from 3-8 independent experiments. nd; below limit of detection for this assay. ns, not significant;

Amino acid sequences for Human (Protein Data Bank accession no. NP 002880) and Murine (NP_082128) Chemerin were aligned and analysed using PeptideCutter to generate predicted trypsin cleavage sites (black vertical lines): The full length sequence in bold and grey is the sequence of PreProChemerin (Seq ID No: 33 for human. and 'Set' ID No: 36 for mouse). The sequence with the N terminal amino acids in grey removed is the ProChemerin sequence (Seq II) No: 32 for human and Seq ID No: 35 for mouse). The sequence in bold, with the N terminal and C-terminal amino acids in grey removed is the sequence of Chemerin (Seq ID No: 31 for human and Seq ID No: 34 for mouse).

Figure 2B:
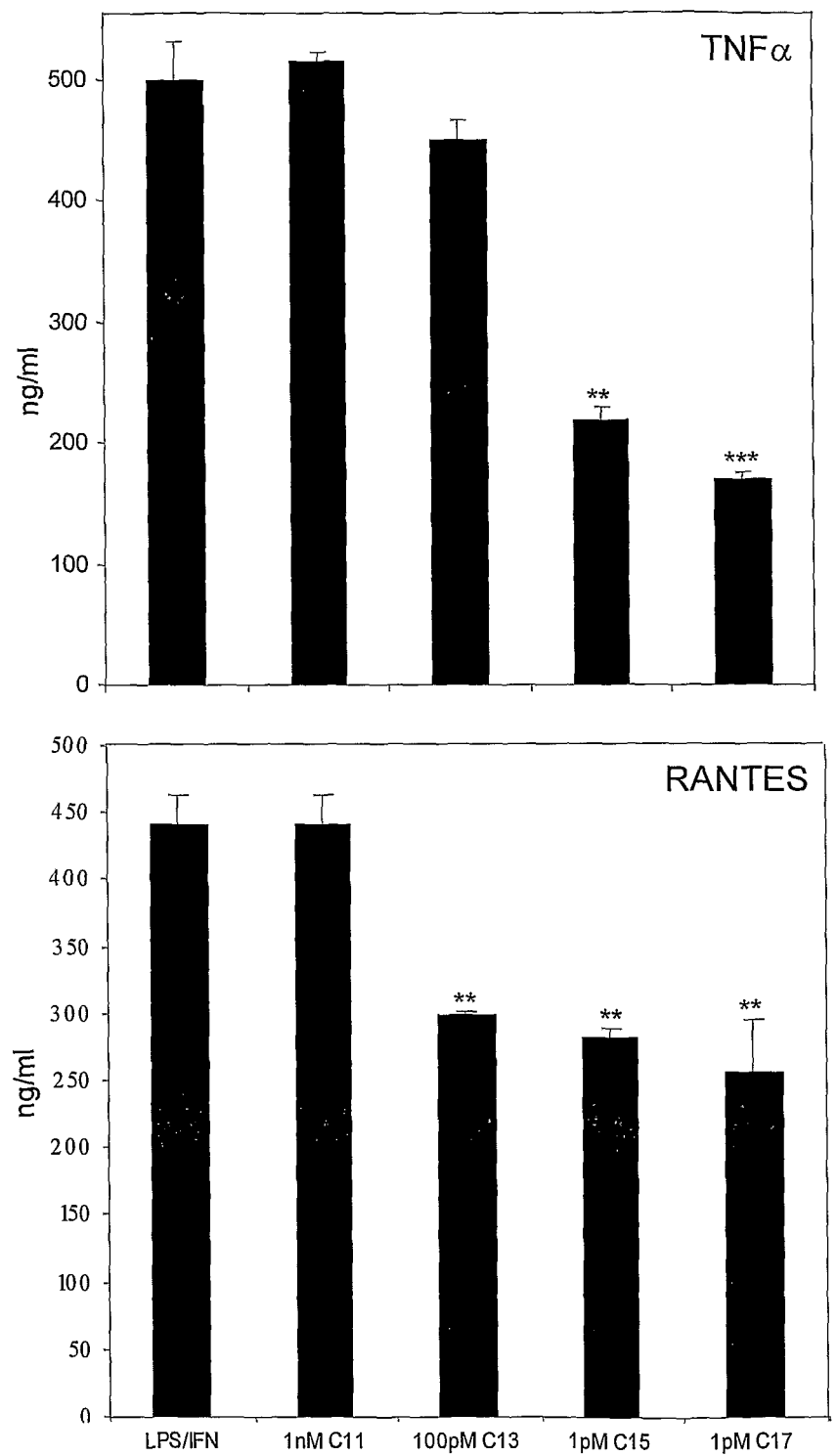
FIG. 2A—shows the amino acid sequence alignment of Human (upper sequence) and Mouse (lower sequence) Chemerin (Tig2).
Figure 3:
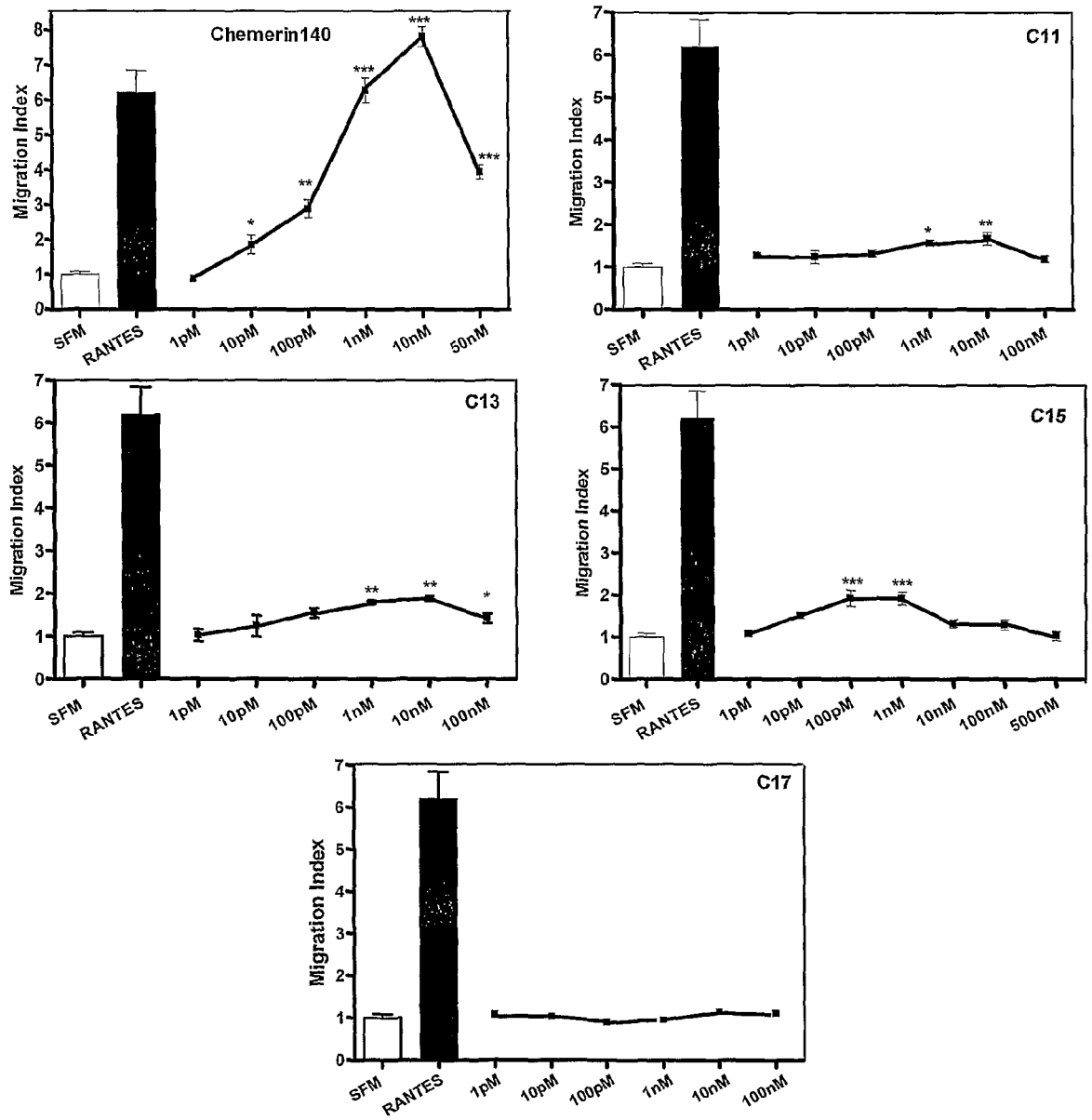
Figure 4:
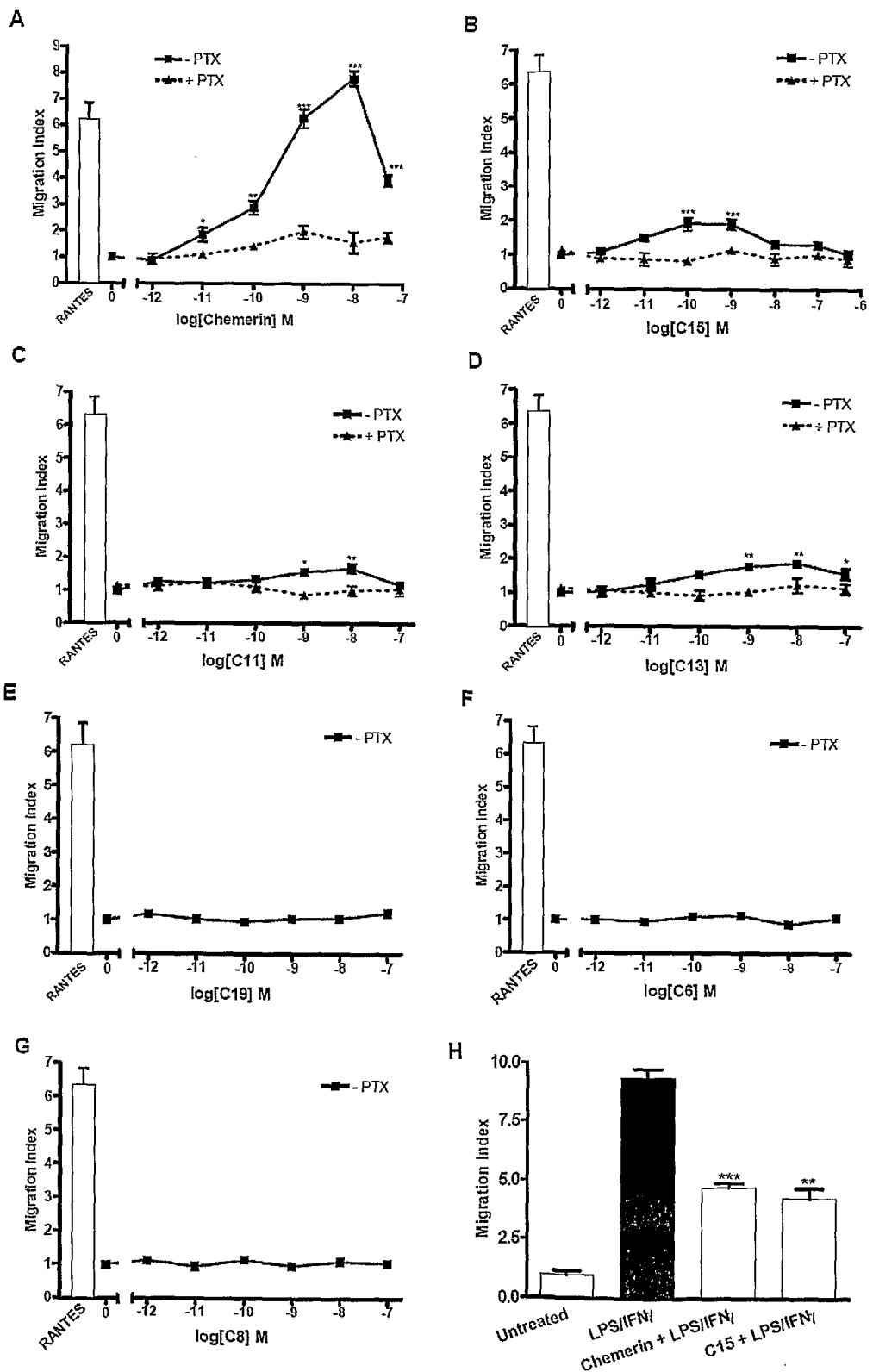
Figure 5:
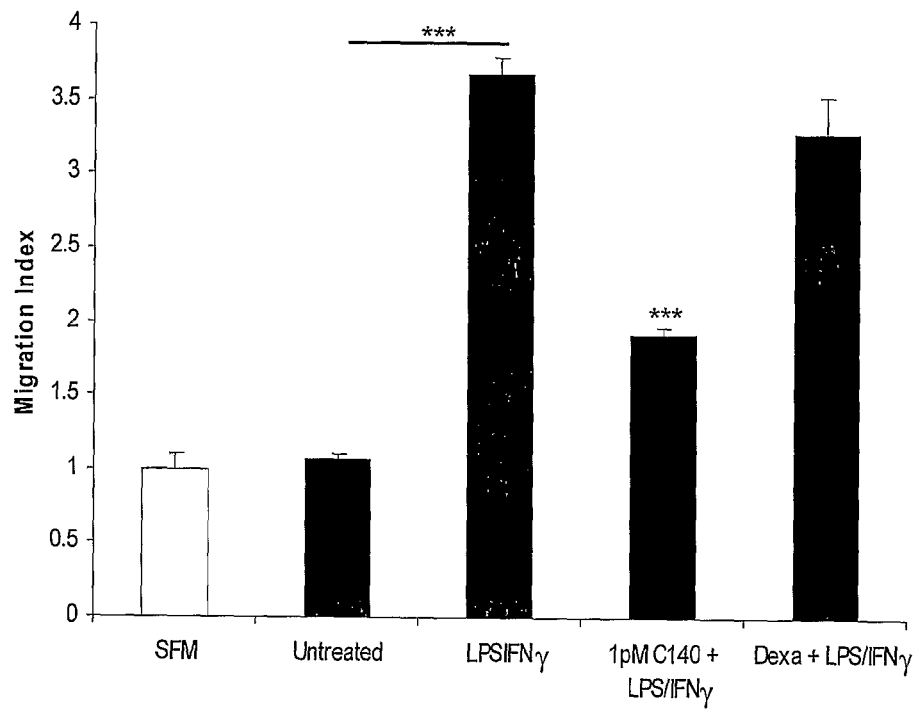
Figure 5:
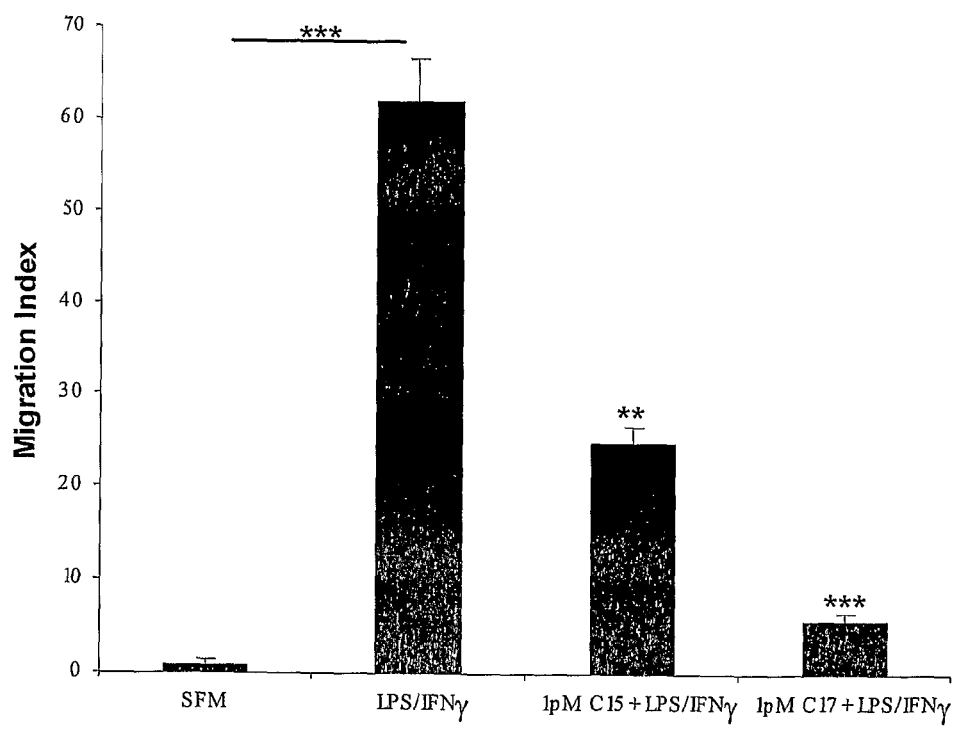
Figure 6:
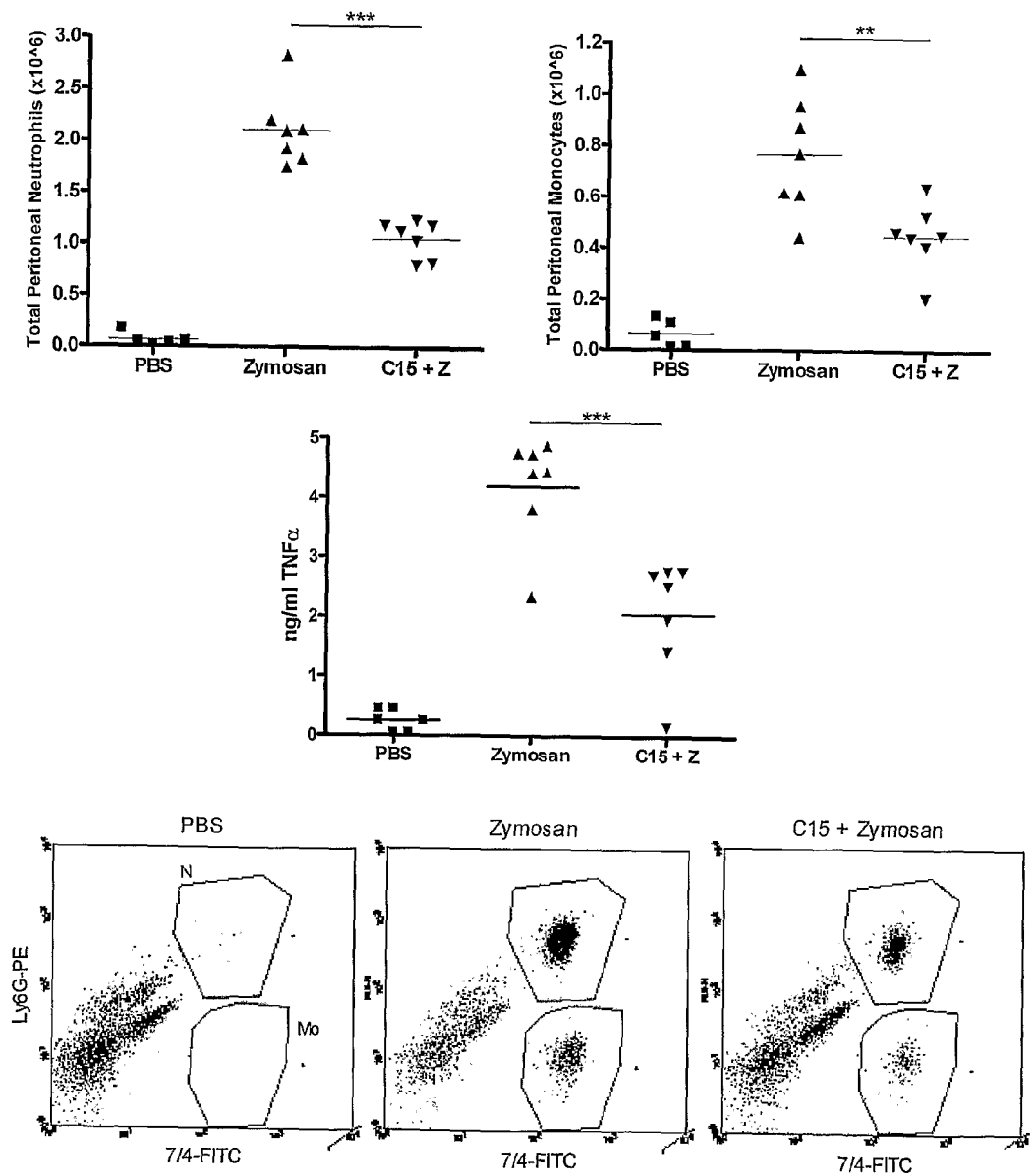
Figure 7:
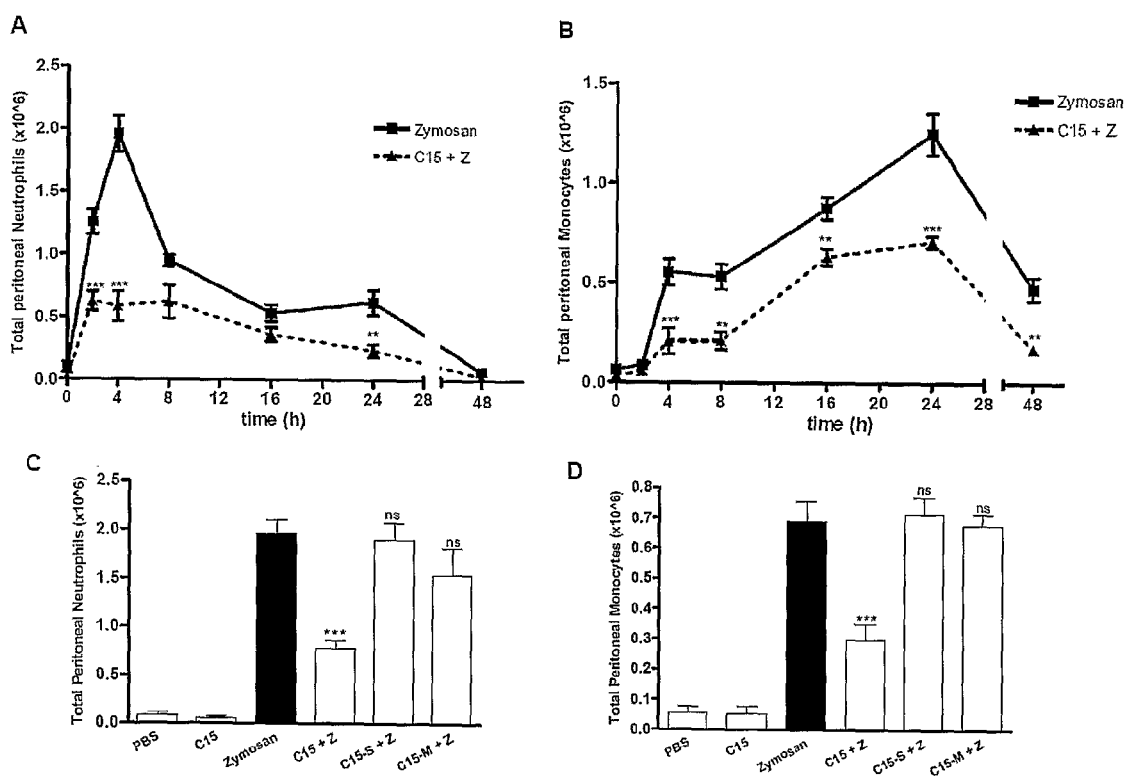
Figure 7:
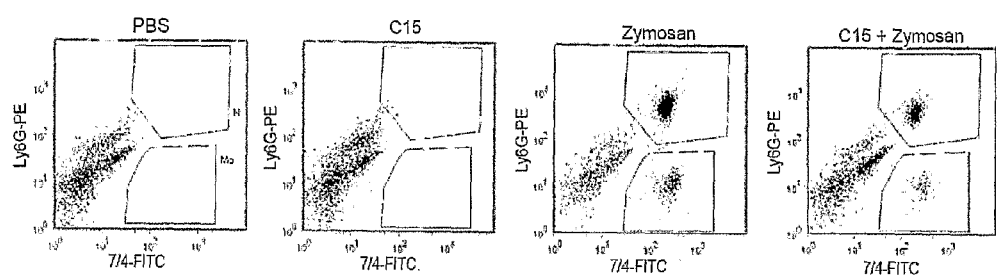
Figure 7:
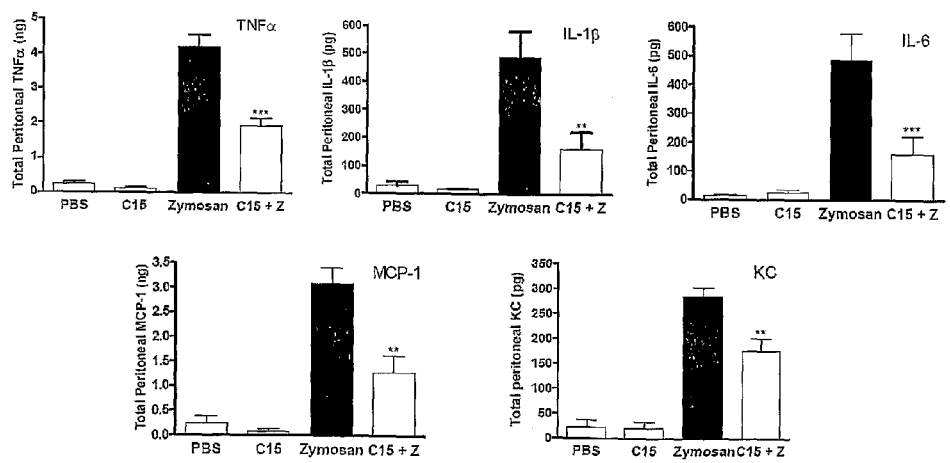
Figure 7:
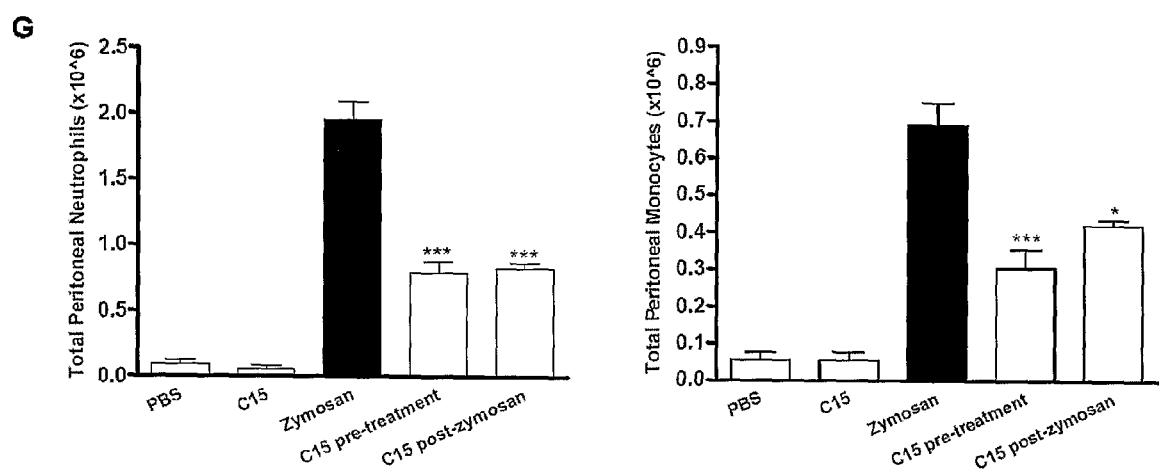

Sequences for C-terminal peptides C11m (Seq ID No: 1), C13m (Seq ID No: 2), C15m (Seq ID No: 3) and C17m (Seq ID No: 4) are also given;

Figure 2A:
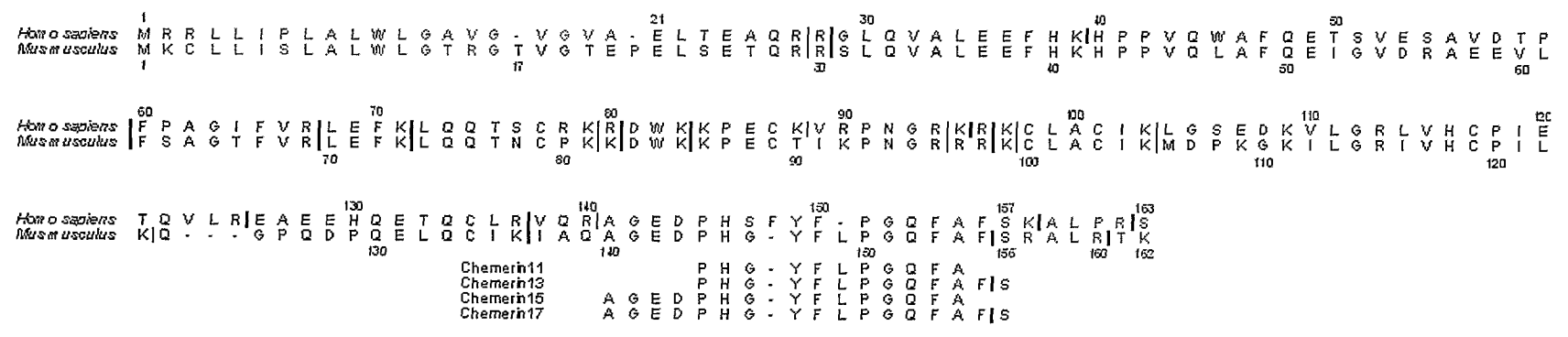

FIG. 2B—illustrates that peptides derived from the C-terminal portion of Chemerin suppress pro-inflammatory mediator production by activated macrophages. Reference in this figure to the peptides C13, C15 and C17 refers to the peptides described previously as C13m, C15m and C17m, respectively;

FIG. 3—illustrates that Chemerin peptides exhibit little macrophage chemotactic properties in comparison to Chemerin140. Reference in this figure to the peptides C11, C13, C15 and C17 refers to the peptides described previously as C11m, C13m, C15m and C17m, respectively;

FIGS. 4A-H—show chemotaxis mediated by chemerin, chemerin peptides and chemerin-treated supernatants. PMΦ ($0.4 \times 10^6$) with or without 30 min Pertussis toxin pre-treatment (PTX; 200 ng/ml) were allowed to migrate towards chemoattractant (FIG. 4A; rmChemerin, FIG. 4B; C15, FIG. 4C; C11, FIG. 4D; C13, FIG. 4E; C19, FIG. 4F; C6, FIG. 4G; C8) in the bottom well of a modified Boyden chamber over 4 h. FIG. 4H—PMΦ ($7.5 \times 10^5$) were allowed to migrate towards conditioned media from untreated macrophages and macrophages treated with LPS/IFNγ±Chemerin or C15 in the bottom well of a modified Boyden chamber over 4 h. Graphs indicate mean Migration Index±SEM for each treatment group (n=4 independent experiments). *, P<0.001; , P<0.01; *, P<0.05 relative to PMΦ+PTX (student's t-test). Reference in this figure to the peptides C11, C13, C15 and C19 refers to the peptides described previously as C11m, C13m, C15m and C19m, respectively;

FIG. 5—illustrates that macrophages exhibit reduced chemotaxis towards conditioned media from Chemerin-treated macrophages. Reference in this figure to the peptides C15 and C17 refers to the peptides described previously as C15m and C17m, respectively;

FIG. 6—illustrates that Chemerin15-mouse suppresses Zymosan-induced peritonitis. Reference in, this figure to the peptide C15 refers to the peptide described previously as C15m. Z refers to Zymosan;

FIGS. 7A-G—shows that chemerin15 ameliorates zymosan-induced peritonitis in mice. FIGS. 7A and 7B—C57B16/J mice were dosed i.p with PBS or chemerin15 (0.32 ng/kg) followed by injection with PBS or zymosan (10 μg, ~$2 \times 10^6$ particles per cavity) 1 h later. Peritoneal exudate cells were harvested by peritoneal lavage at multiple time points (FIGS. 7A and 7B; 5-6 mice/treatment) or after 4 h (FIGS. 7C-7E; 6-15 mice/group). FIGS. 7C-7E—total cell numbers in lavage fluid were quantified and cellular composition (neutrophils vs mononuclear phagocytes) determined using FACS analysis. Cells were blocked with 2.4G2 anti-FcγRII/III and stained with Ly-6G-PE and 7/4-FITC. Gates were constructed around two populations, the neutrophils (N; 7/4high, Ly-6Ghigh) and inflammatory monocytes (Mo; 7/4high, Ly-6Glow). FIG. 7E—representative FACS plots are shown for each treatment group at 4 h post-zymosan. FIG. 7F—peritoneal lavage fluid was assayed for TNFα and KC by ELISA and IL-6, IL-1β and MCP-1 by Luminex assay. C15; Chemerin15, Z; Zymosan. *, P<0.001; , P<0.01 ** relative to zymosan-treated animals (Student's t test). FIG.

Figure 8:
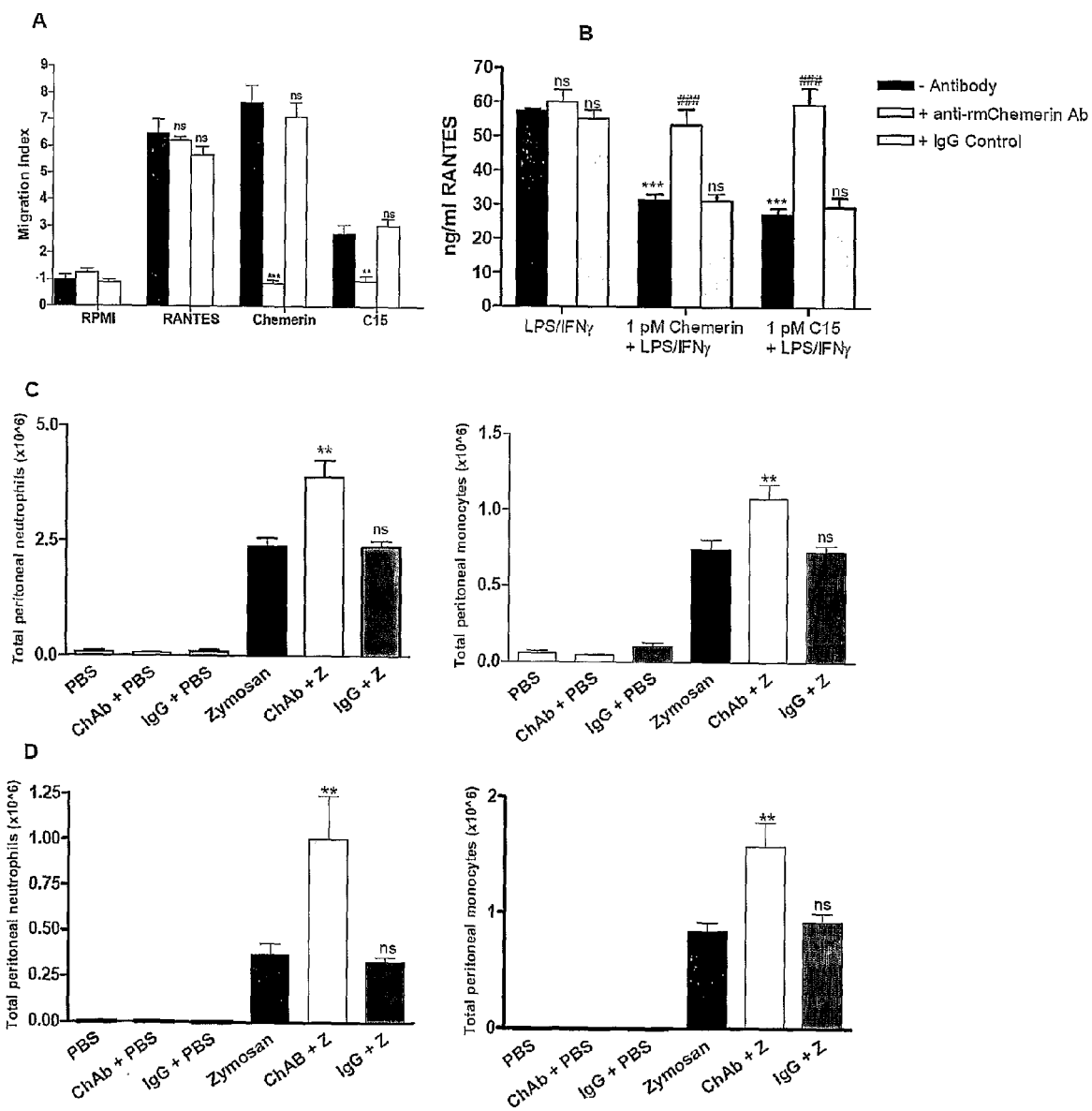
Figure 9:
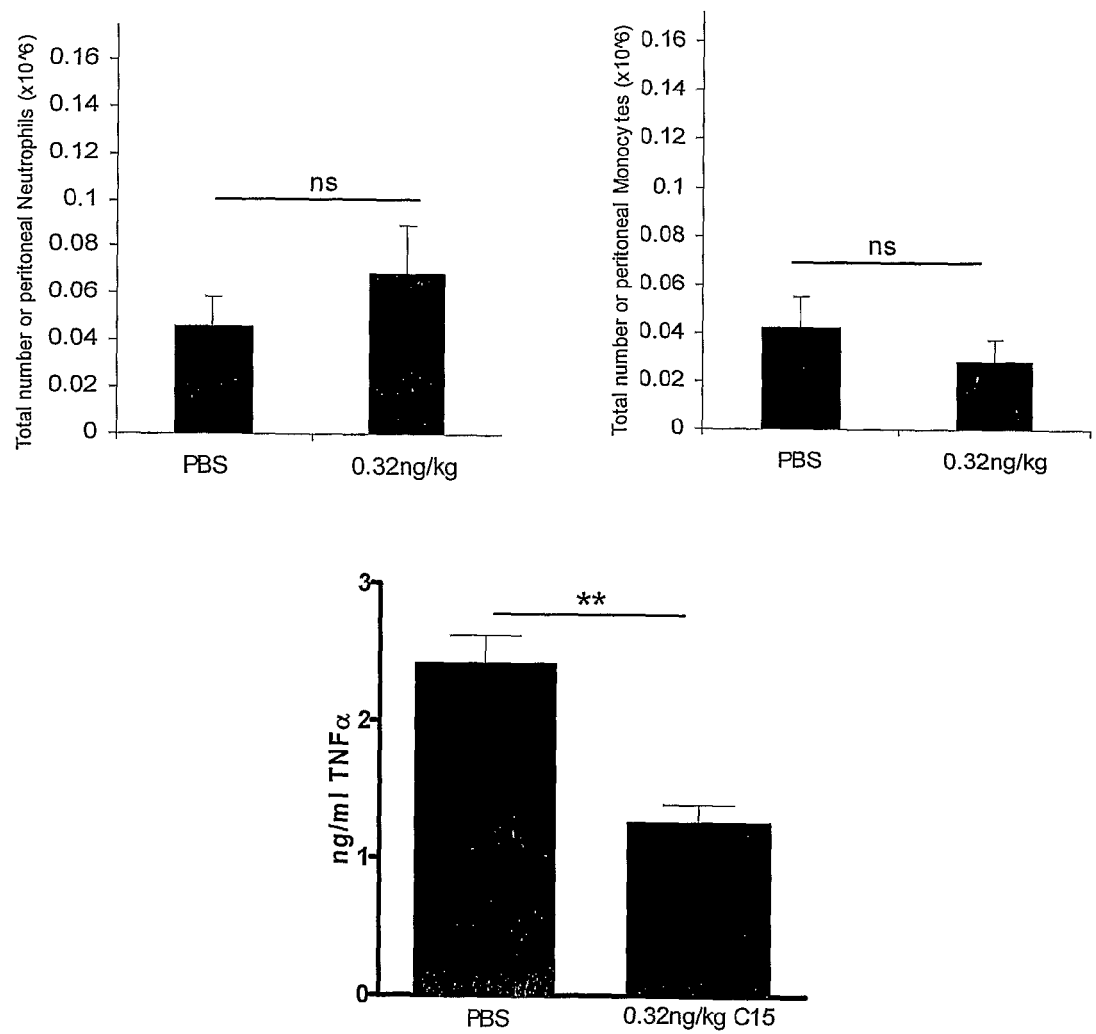
Figure 10:
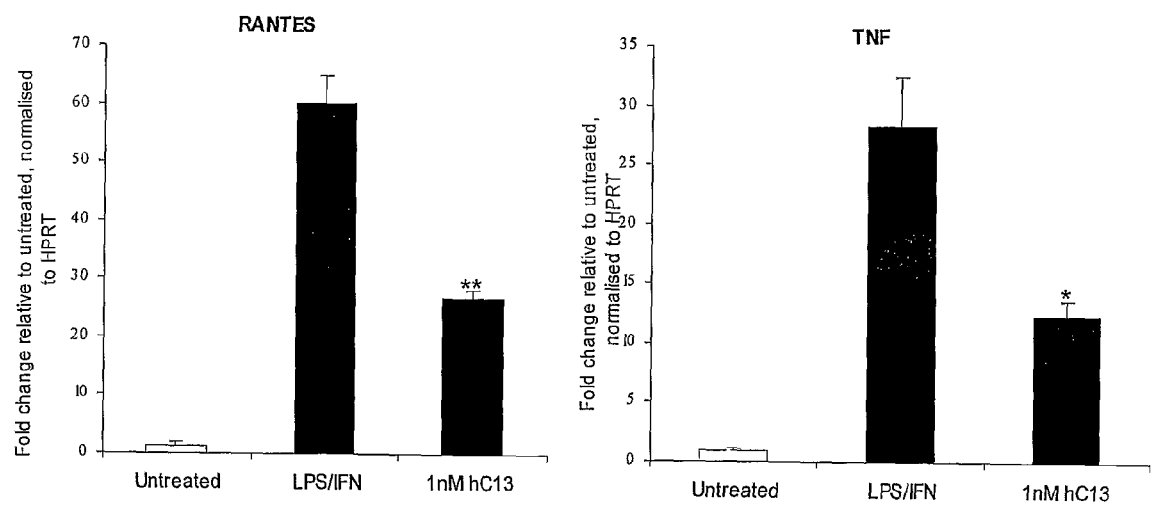
Figure 11:
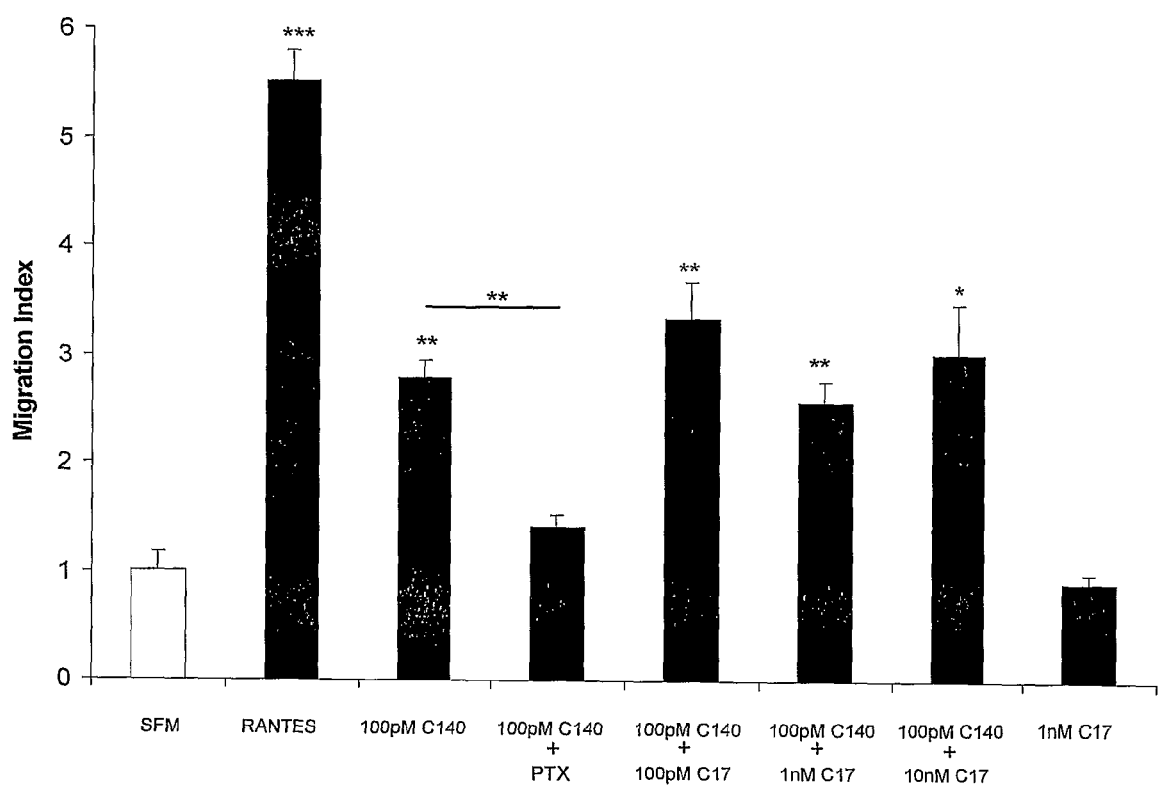
Figure 12:
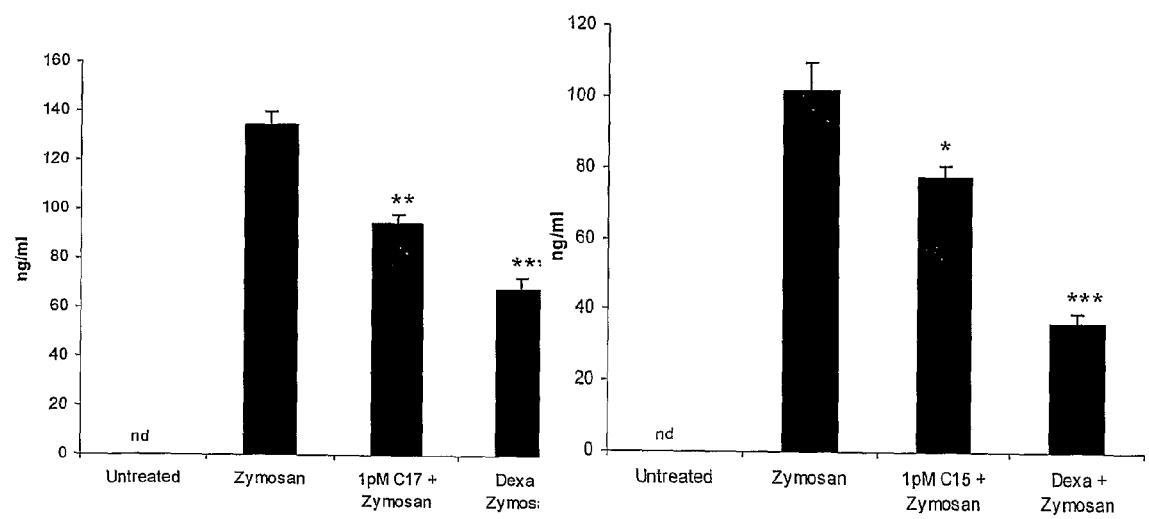
Figure 13:
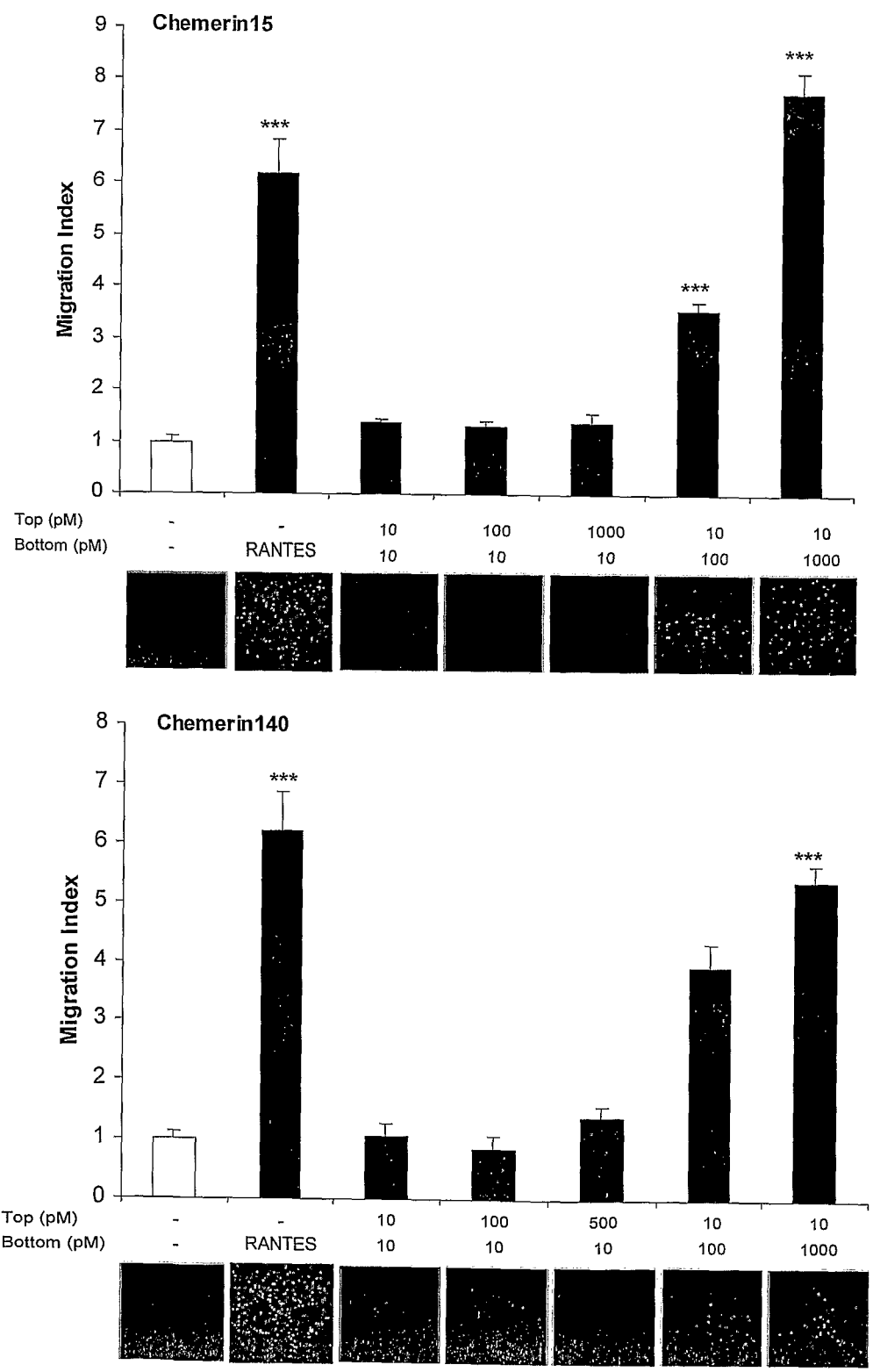
Figure 14:
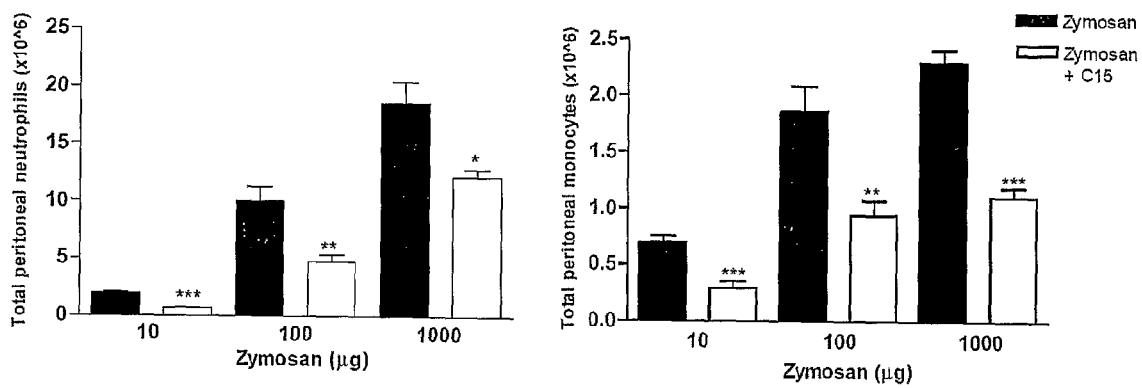
Figure 14:
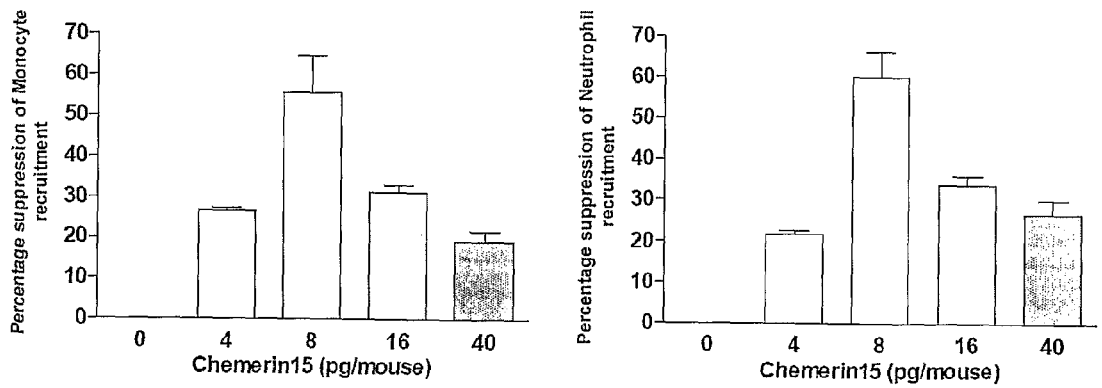

7G—Mice (6-8/treatment) were dosed i.p with zymosan (10 µg) and with C15 (8 pg) or PBS either 1 h beforehand (C15 pre-treatment) or 2 h later (C15 post-treatment). Peritoneal lavage was carried out 4 h post-zymosan challenge. Reference in this figure to the peptide C15 refers to the peptide described previously as C15m;

FIGS. 8A-D—shows that anti-chemerin antibody neutralizes chemerin species and exacerbates peritoneal inflammation. FIG. 8A—PMΦ were used in macrophage chemotaxis assays (performed as detailed in FIG. 7) and allowed to migrate toward RANTES, chemerin or C15 with or without anti-rmChemerin antibody or control IgG. Graphs indicate mean Migration Index±SEM for each treatment group (n=4 independent experiments). *, $P<0.001$; , $P<0.01$; *, $P<0.05$ relative to chemoattractant. FIG. 8B—PMΦ were pretreated with 1 pM C15 or 1 pM chemerin with or without anti-rmChemerin antibody or control IgG for 1 h and then stimulated with LPS (100 ng/ml) and IFNγ (20 ng/ml) for 15 h. Mean expression of RANTES±SEM in macrophage supernatants after 16 h was determined by ELISA (n=4 independent experiments). **, $P<0.01$; *, $P<0.05$ relative to LPS/IFNγ-treated samples. FIGS. 8C and 8D—C57B16/J mice were dosed i.p with PBS, anti-rmChemerin antibody (100 ng/mouse) or control IgG (100 ng/mouse) followed by injection with PBS or zymosan (10 µg/cavity) 1 h later. Peritoneal exudate cells were harvested by peritoneal lavage 4 h and 24 h post-zymosan injection and processed as outlined in FIG. 7. Z; zymosan, ChAB; anti-rmChemerin antibody. **, $P<0.01$ relative to zymosan-challenged mice. Reference in this figure to the peptide C15 refers to the peptide described previously as C15m;

FIG. 9—illustrates that injection of 0.32 ng/kg C15m alone does not induce neutrophil or macrophage recruitment but does reduce peritoneal TNFα levels. Reference in this figure to the peptide C15 refers to the peptide described previously as C15m;

FIG. 10—illustrates that a modified Chemerin13-human peptide suppresses RANTES and TNFα transcript expression in murine macrophages. Reference in this figure to the peptide hC13 refers to the modified C13h peptide;

FIG. 11—illustrates that C17m does not affect C140-induced macrophage chemotaxis. Reference in this figure to the peptide C17 refers to the peptide described previously C17m;

FIG. 12—illustrates that Chemerin15-mouse and Chemerin17-mouse suppress TNFα secretion by murine macrophages stimulated with Zymosan. Reference in this figure to the peptides C15 and C17 refers to the peptides described previously as C15m and C17m, respectively. Dexa refers to dexamethasone;

FIG. 13—is a checkerboard analysis demonstrating that Chemerin140 and Chemerin15-mouse induce true macrophage chemotaxis and not chemokinesis. Reference in this figure to the peptide C15 refers to the peptide described previously as C15m;

FIGS. 14A-B—shows that chemerin15 suppresses monocyte and neutrophil recruitment in zymosan peritonitis over a range of C15 and zymosan doses. FIG. 14A—C57B16/J mice (5-6 animals/treatment) were dosed i.p with PBS or C15 (0.32 ng/kg) followed by injection with PBS or zymosan dose range (10 µg-1 mg; A) 1 h later. FIG. 14B—Mice (5-6 animals/treatment) were dosed i.p with PBS or C15 dose range (4-40 pg/mouse followed by injection with PBS or zymosan (10 µg; $2 \times 10^6$ particles/cavity) 1 h later Peritoneal exudate cells were harvested by peritoneal lavage 4 h post-zymosan challenge; 5-6 mice/group). Total cell numbers in lavage fluid were quantified and cellular composition (Neutrophils vs mononuclear phagocytes) determined using FACS analysis as described in FIG. 7. C15; Chemerin15, Z; Zymosan. *, $P<0.001$; , $P<0.01$ **; $P<0.05$ * relative to zymosan-treated animals Student's t test). Reference in this figure to the peptide C15 or chemerin15 refers to the peptide described previously as C15m; and FIG. 15—shows fluorimetry for zymosan recognition by macrophages expressed as relative recognition index. Experiments were performed in the presence or absence of various concentrations of C15. Data represent mean (±s.e.m.) of four pooled, normalized experiments.

Reference herein to Chemerin140 or C140 is reference to the 140 amino acid mouse Chemerin protein (Chemerin-140-mouse) of Sequence ID no: 34.

DETAILED DESCRIPTION

Examples

Chemerin140 Exerts Anti-Inflammatory Effects on Activated Macrophages which are Abrogated by Protease Inhibitors Previous studies have demonstrated that serine proteases released by polymorphonuclear cells (PMN) following degranulation cleave the C-terminal extremity of ProChemerin and release its chemotactic potential (Wittamer V et al. J Immunol. Jul. 1, 2005; 175(1):487-493). However, the anti-inflammatory effect of peptides produced by further proteolytic processing of Chemerin is novel and inventive.

Murine peritoneal macrophages (PMθ, also referred to as PMΦ herein) were cultured under various conditions: Untreated; LPS (100 ng/ml) and IFNγ (20 ng/ml) for 15 h; Chemerin (1 pM) pre-treatment for 1 h then LPS/IFNγ for 15 h; Leupeptin (protease inhibitor; 15 mg/ml) and Chemerin (1 pM) for 1 h then LPS/IFNγ for 15 h; or Dexamethasone (positive control; 1 µM pre-treatment for 1 h then LPS/IFNγ for 15 h.

Figure 1A:
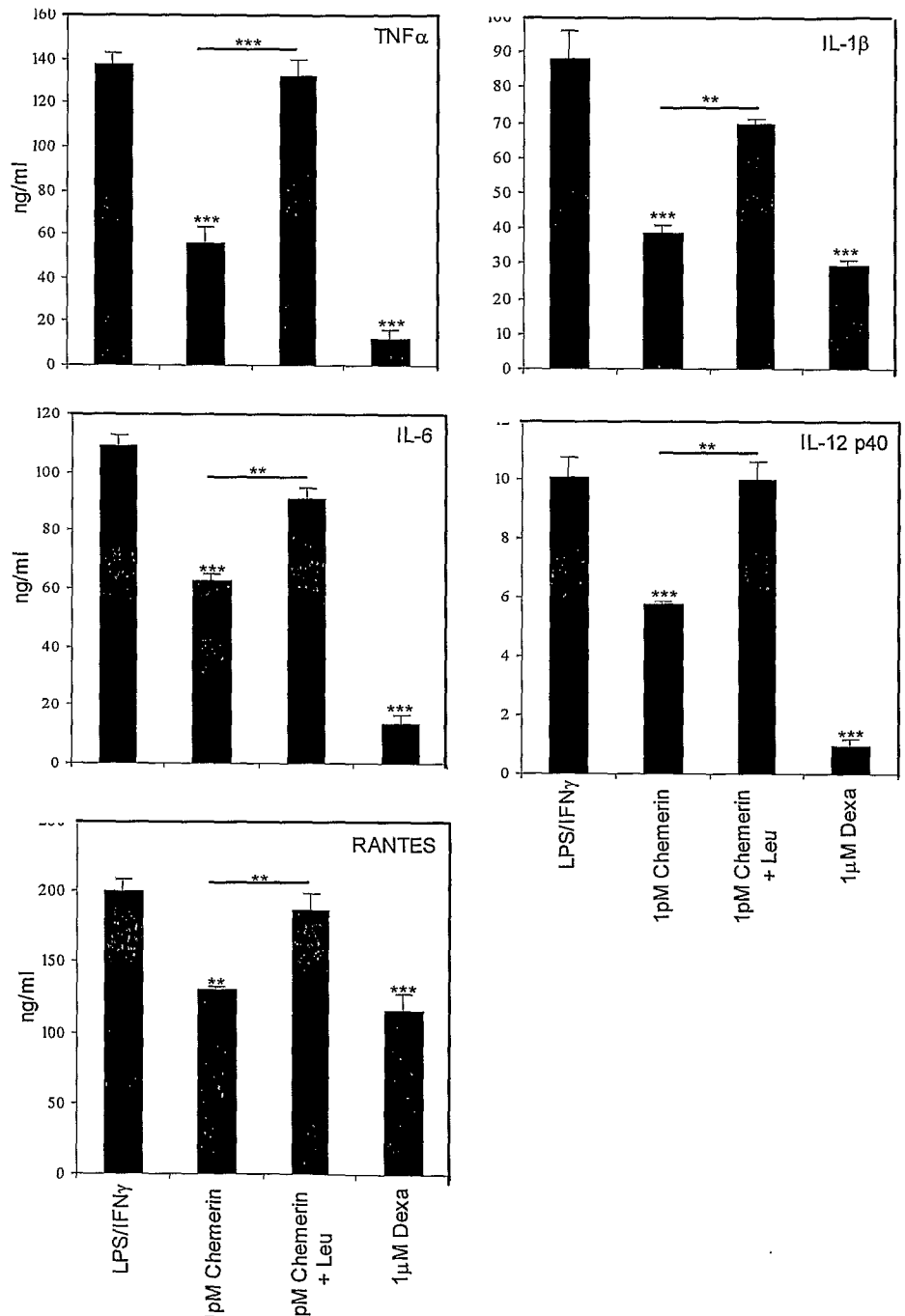
FIGS. 1A-F—FIGS. 1A and 1B illustrate that Chemerin140 suppresses production of inflammatory mediators by macrophages in a proteolysis dependent fashion. Supernatants from macrophages or activated macrophages (treated with 100 ng/ml LPS and 20 ng/ml interferon gamma were assayed for cytokine expression using Luminex and ELISA assays. Cells were incubated in the presence or absence of recombinant murine chemerin or dexamethasone at the indicated doses and in the absence or presence of the protease inhibitor leupeptin (15 mg/ml).
Figure 1B:
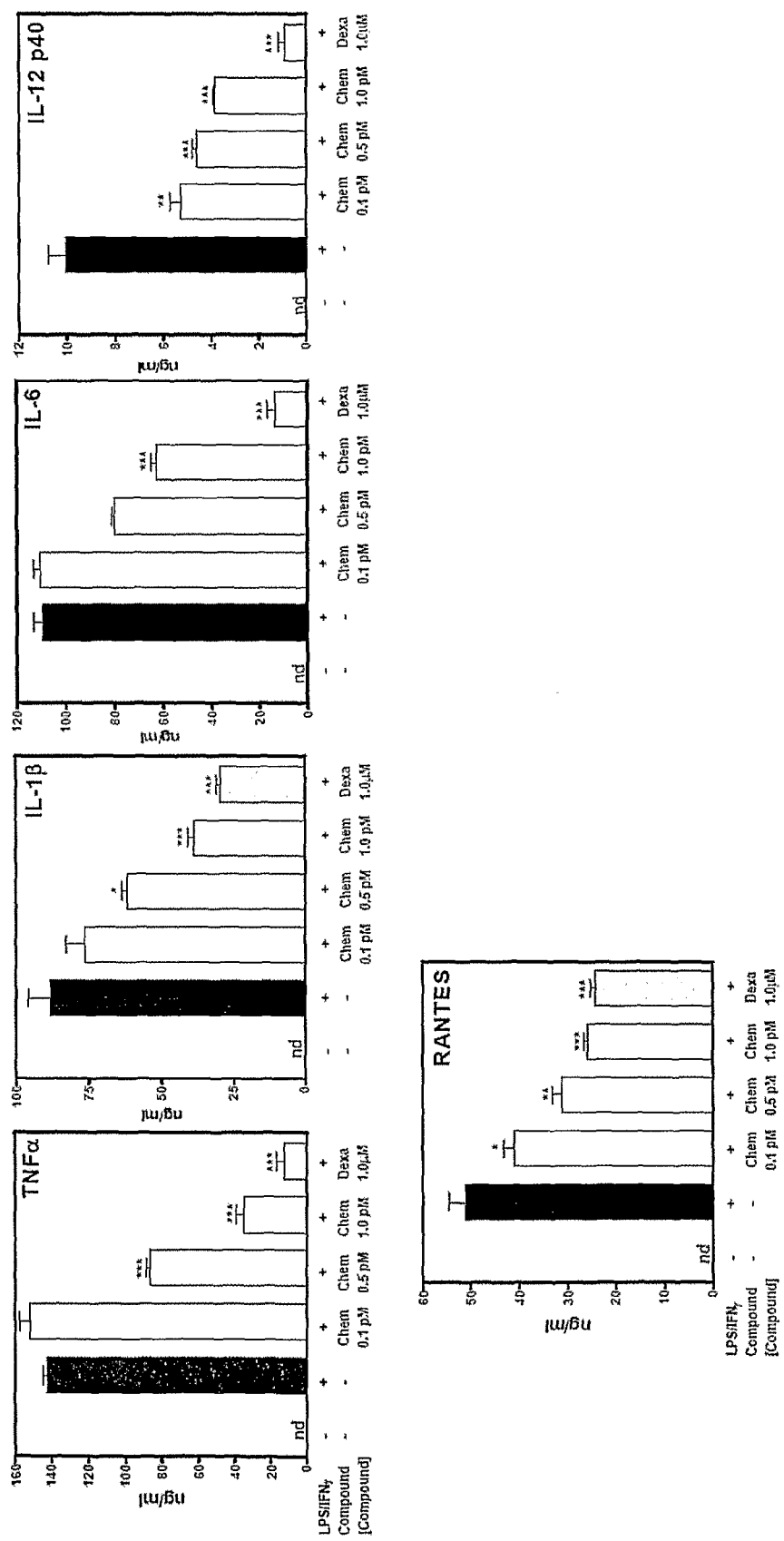

Supernatants from the Chemerin+lipopolysaccharide/interferon-γ (LPS/IFNγ)-treated macrophages were analysed for chemokine content and the results showed that chemerin treated cells displayed significantly lower levels of TNFα (70%), IL-12 p40 (54%), RANTES (CCL5; 40%), IL-6 (42%) and IL-1β (60%) compared to LPS/IFNγ-treated samples (n=5; p<0.001 FIGS. 1A and 1B). This anti-inflammatory effect was inhibited by broad-spectrum protease inhibitors (leupeptin), which when added to the macrophages prevented any anti-inflammatory effect, illustrating the importance of additional Chemerin cleavage in the production of these anti-inflammatory peptides (FIG. 1A and FIG. 1F).

It was further demonstrated that these effects were Chemerin-specific by using an anti-Chemerin neutralizing antibody; which removed the anti-inflammatory effect of the Chemerin (FIG. 8B).

The bar graphs in FIG. 1A show the mean expression of cytokines as determined by the Luminex assay±SEM. Experiments were performed with triplicate determinations for each treatment. Representative data from three independent experiments employing cells from different groups of C57B16/J mice are shown. p<0.001 *; p<0.01  relative to LPS/IFNγ-treated samples unless otherwise stated. Dexa refers to Dexamethasone (1 mM).

FIG. 1B shows similar results as discussed above in regard to FIG. 1A, with additional data showing the effects of chemerin at different concentrations of 0.1 pM, 0.5 pM and 1.0 pM.

Figure 1C:
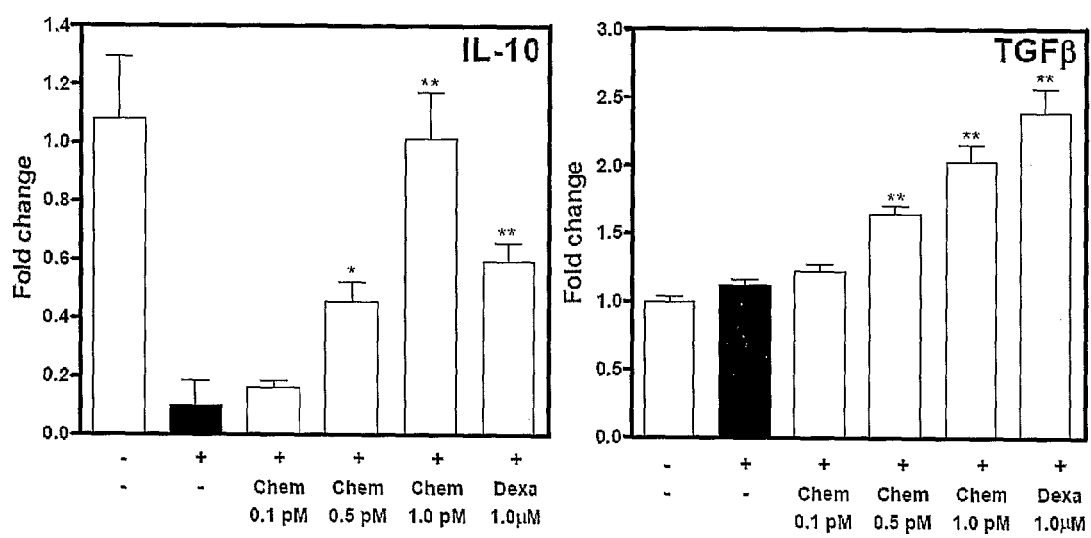

In addition, FIG. 1C shows that chemerin induced the expression of mRNA for the anti-inflammatory cytokines TGFβ (54%) and IL-10 (89%).

Figure 1D:
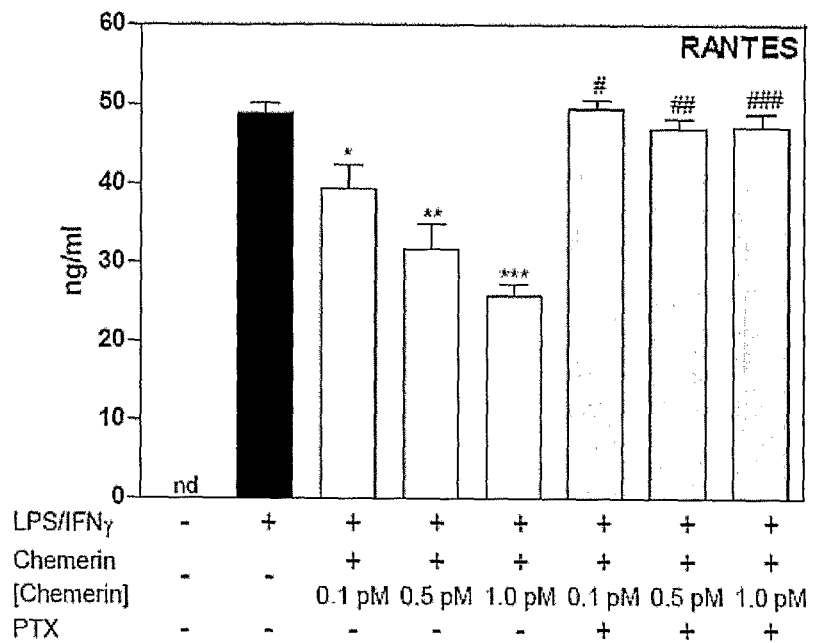

The effects of chemerin were dose-dependent with maximal responses observed at 1 pM (FIG. 1B and FIG. 1C), and were pertussis toxin-sensitive, indicating the involvement of a Gαi-linked GPCR (FIG. 1D).

Figure 1E:
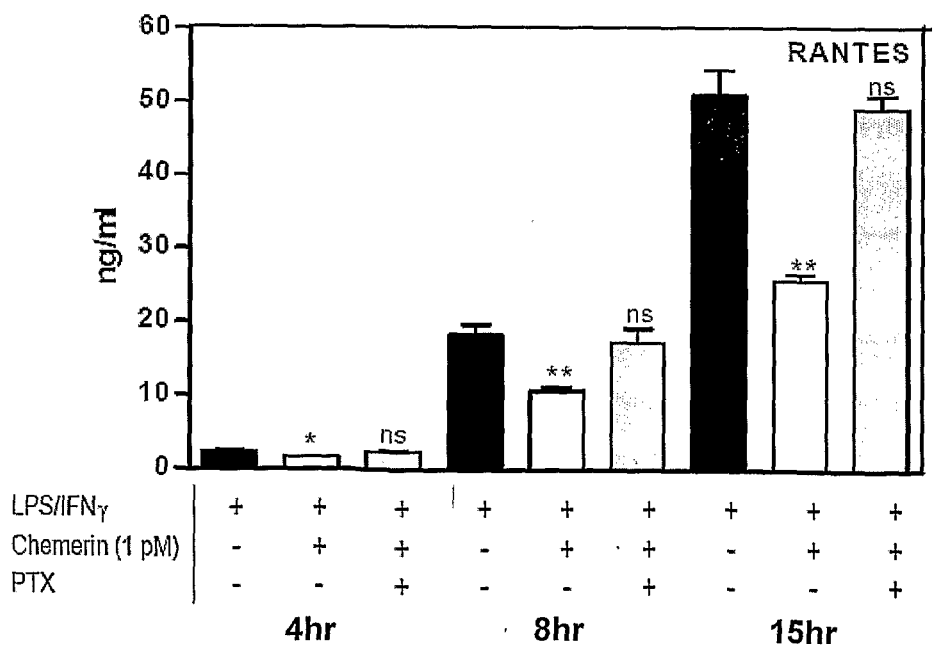
Figure 1F:
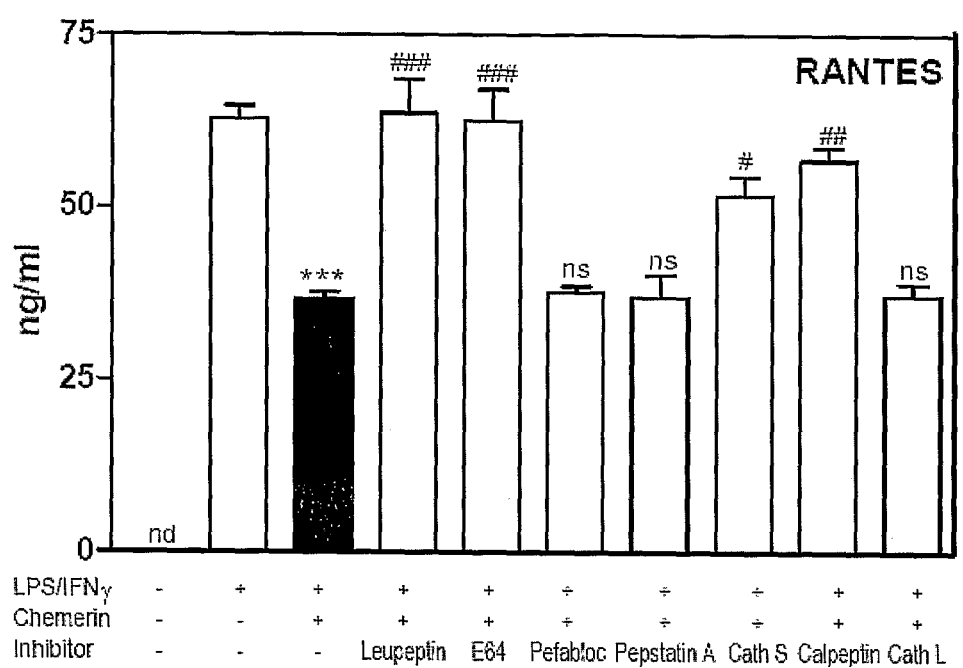

In addition, anti-inflammatory effects were observed at 4 h, 8 h, and 15 h after LPS/IFN? administration and were abrogated by PTX at all time points (FIG. 1E).

Previous studies have demonstrated that serine proteases released by granulocytes following degranulation cleave the C-terminal extremity of prochemerin and release its chemotactic potential (Wittamer, V., et al., (2005), *J Immunol* 175: 487-493). The possibility that murine chemerin could undergo further proteolytic processing by enzymes released upon murine MΦ activation was investigated. As discussed above in relation to FIG. 1A, coadministration of chemerin with Leupeptin (a serine and cysteine protease inhibitor) abolished its anti-inflammatory effects (FIG. 1A and FIG. 1F). This effect was also demonstrated for E-64 (a cysteine protease inhibitor), whilst the acidic protease inhibitor Pepstatin A and the serine protease inhibitor Pefabloc exerted no effect on chemerin-mediated suppression of MΦ activation (FIG. 1F). These data demonstrate that chemerin exerts inhibitory effects on MΦ activation in a cysteine protease-dependent manner. A cathepsin L inhibitor (Z-FF-FMK), cathepsin S inhibitor (Z-FL-COCHO) and a calpain I and II inhibitor, calpeptin were used to further probe the specific cysteine proteases involved in chemerin cleavage (FIG. 1F). It was found that chemerin's anti-inflammatory effects were dependent upon calpains and cathepsin S but was independent of cathepsin L. Taken together the results demonstrate for the first time that classically activated murine MΦ are capable of converting chemerin into potent peptide inhibitors of MΦ activation by specific cysteine protease-mediated cleavage of the parent molecule, most likely involving calpain II and cathepsin S.

C-terminal Chemerin Peptides with Anti-Inflammatory Activity

A series of 11-20aa peptides were designed using sequence alignment functions in Ensembl as an indicator of important conserved residues and named C11m (P144-A154; PHGYFLPGQFA Seq ID No: 1), C13m (P144-S156; PHGYFLPGQFAFS Seq ID No: 3), C15m (A140-A154; AGEDPHGYFLPGQFA Seq ID No: 4) and C17m (A140-S156; AGEDPHGYFLPGQFAFS Seq ID No: 6) C19 (A138-S156; AQAGEDPHGYFLPGQFAFS Seq ID No: 37), N19 (E23-K41; ELSETQRRSLQVALEEFHK Seq ID No: 44) and M20 (K86-K105; KPECTIKPNGRRRKCLACIK Seq ID No: 45). FIG. 2A shows a sequence alignment for some of these peptides. Chemerin peptides (1 pM-100 nM) were characterized in the macrophage activation assay according to the described protocol.

Murine PMθ were cultured under various conditions: Untreated, LPS (100 ng/ml) and IFNγ (20 ng/ml) for 15 h; Chemerin peptides (at a concentration of 1 pM-100 nM) pre-treatment for 1 h then LPS/IFNγ for 15 h. The concentrations displayed represent the optimal effective doses for each peptide in both assays. The bar graphs in FIG. 2B displays mean expression of RANTES and TNFα protein±SEM. Experiments were performed with triplicate determinations for each treatment. Representative data from five independent experiments employing cells from different groups of C57B16/J mice are shown. p<0.01 ; p<0.001 * relative to LPS/IFNγ treated samples.

C-terminal peptides C13m (100 pM), C15m (1 pM) and C17m (1 pM) suppressed LPS/IFNγ-induced RANTES secretion (C13m—32%; C15m—41%; C17m—49%) and TNFα expression (C13m—10%; C15m—56%; C17m—66%, FIG. 2B). C15m and C17m inhibited macrophage activation to a similar extent as C140 when used at the same concentration.

Similar results are shown in Table 1, where C-terminal peptides C13 and C19 moderately suppressed LPS/IFNγ-induced RANTES and TNFα expression with an optimal dose of 100 pM (Table 1). Chemerin15 (C15), however, retained the anti-inflammatory activity shown by proteolysed chemerin and inhibited cytokine expression with similar efficacy and potency as chemerin (optimal dose 1 pM). In addition, C11, the N-terminal peptide (N19), midstream peptide (M20), and the control peptides (scrambled C15; C15-S, GLFHDQAGPPAGYEF; Seq ID No: 39, and mutant C15; C15-M, AGEDPHGYALPGQAA; Seq ID No: 40) were devoid of anti-inflammatory activity in the MΦ activation assay. It was also found that the 6 aa (RALRTK; Seq ID No: 41) and 8 aa (FSRALRTK; Seq ID No: 42) peptides removed during prochemerin cleavage by proteases of the coagulation and fibrinolytic cascades, named C6 and C8, respectively, possessed no detectable anti-inflammatory activity in the MΦ activation assay.

TABLE 1

Percentage inhibition of LPS/IFNγ - induced inflammatory cytokine expression

| Cytokine | Chemerin | C6 | C8 | C11 | C13 | C15 | C15-S | C15-M | C19 | N19 | M20 |
|---|---|---|---|---|---|---|---|---|---|---|---|
| TNFα | 70 | 0 | 0 | 0 | 10 | 61 | 0 | 0 | 21 | 0 | 0 |
| RANTES | 40 | 0 | 0 | 0 | 32 | 47 | 0 | 0 | 41 | 0 | 0 |
| IL-1β | 60 | — | — | — | — | 54 | — | — | — | — | — |
| IL-12 p40 | 54 | — | — | — | — | 47 | — | — | — | — | — |
| IL-6 | 42 | — | — | — | — | 43 | — | — | — | — | — |

With reference to Table 1, anti-inflammatory activity of chemerin-derived peptides—Murine PMΦ were cultured as described for FIG. 1B and were challenged with LPS (100 ng/ml) and IFNγ (20 ng/ml) for 15 h with/without pre-treatment with peptides (0.1 pM-100 nM) for 1 h. Where peptides exhibited anti-inflammatory properties, percentage inhibition of LPS/IFNγ-induced macrophage activation represents effect with optimal dose (1 pM Chemerin and C15 or 100 pM C13 and C19). Peptide sequences are: C11 (P144-A154; PHGYFLPGQFA), C13 (P144-S156; PHGYFLPGQFAFS), C15 (A140-A154; AGEDPHGYFLPGQFA), C19 (A138-S156; AQAGEDPHGYFLPGQFAFS; Seq ID: No. 37), N19 (E23-K41; ELSETQRRSLQVALEEFHK Seq ID No: 44) and M20 (K86-K105; KPECTIKPNGRRRKCLACIK Seq ID No. 45). Control peptides: scrambled C15 (C15-S; GLFHDQAGPPAGYEF) and mutant C15 (C15-M; AGEDPHGYALPGQAA; F148A & F153A). Data represent mean percentage inhibition of cytokine production by classically activated macrophages from 4-8 independent experiments as determined by ELISA and Luminex assay.

Chemerin140, but not its C-Terminal Derived Anti-Inflammatory Peptides, is a Potent Macrophage Chemoattractant Modified Boyden-chamber assays were utilized to demonstrate the macrophage chemoattractant properties of C140. Mouse Chemerin140 exhibits a typical bell-shaped curve with optimal chemotaxis observed at nM, declining thereafter, presumably following receptor desensitization or breakdown of the chemoattractant gradient (FIG. 3). This is also shown in FIG. 4A, with additional data showing the effects of Pertussis toxin pre-treatment (PTX: 200 ng/ml).

PMθ ($0.5 \times 10^6$) were allowed to migrate towards chemoattractant (Chemerin140 or Chemerin peptides) in the bottom well of a modified Boyden chamber over 4 h. Filters were fixed in 4% formalin, then migrated cell nuclei were stained with DAPI and visualised. Serum free media (SFM) were used as a negative control and the macrophage chemoattractant RANTES (25 ng/ml; 3 nM) as a positive control. The graphs indicate mean Migration Index (Chemoattractant % threshold area/SFM % threshold area)±SEM for each treatment group (n=5-6). $p<0.001$ *; $p<0.01$ ; $p<0.05$ * relative to SFM treated wells.

C11m, C13m and C15m (1 pM-100 nM) were observed to possess little chemotactic activity in comparison to C140 (1 pM-50 nM) or positive control the CC chemokine RANTES (25 ng/ml; 3 nM). Maximal macrophage migration was observed at 100 pM C15m and 10 nM C13m and C11m. C17m, however, displayed no chemotactic activity at all concentrations tested (0.1 pM-500 nM; n=5 independent experiments; (FIG. 3). This result is also shown in FIGS. 4B-D, with additional data showing the effects of Pertussis toxin pre-treatment (PTX: 200 ng/ml). With reference to FIG. 4E, C19 also displayed no chemotactic activity at all concentrations tested (0.1 pM-500 nM; FIG. 4E). Thus a chemerin-derived peptide has been identified that retains anti-inflammatory activity but exhibits no chemotactic activity for MΦs, indicating the existence of distinct function-specific components of chemerin that could be exploited therapeutically. The prochemerin-derived peptides, C6 and C8, which were found to be devoid of MΦ anti-inflammatory activity, were also incapable of inducing MΦ migration at all concentrations tested (0.1 pM-500 nM; FIG. 4F-G). The data appears to therefore indicate that the principal chemotactic species is either the cleaved chemerin molecule itself, or an as yet unidentified peptide.

Additional Example Showing Chemerin and Chemerin15 Induce Generalized Suppression of Chemoattractant Production by Macrophages Given the well established role of MΦ-derived chemoattractants in the recruitment of immune cells during inflammation (Glabinski, A. R., et al., (1998). *Neuroimmunomodulation* 5:166-171; Huang, D. J. et al., (2001). *J. Exp. Med.* 193:713-726), conditioned media was used from untreated MΦ and MΦ treated with chemerin+LPS/IFNγ, C15+LPS/IFNγ and LPS/IFNγ alone in chemotaxis assays to assess how suppression of MΦ activation by chemerin and the synthetic C-terminal peptide, C15 might affect further MΦ recruitment (See FIG. 4H). Untreated MΦ-conditioned medium itself exhibited no chemotactic activity for MΦ (Migration index 1.0±0.15); however, LPS/IFNγ-treated macrophage medium induced a marked increase in MΦ chemotaxis (Migration index 9.3±0.4; FIG. 4H). Furthermore, MΦs exhibited reduced chemotaxis towards conditioned media from chemerin+LPS/IFNγ and C15+LPS/IFNγ-treated macrophages by 49% and 55%, respectively (FIG. 4H). This indicates that chemerin and C15 induce general suppression of a broad range of MΦ-derived MΦ chemoattractants to the extent that the chemotactic activity of the conditioned media is affected.

Further secondary chemotaxis assays revealed suppressed macrophage chemotaxis towards supernatants from Chemerin140-mouse, Chemerin15-mouse and Chemerin17-mouse-treated macrophages. These results show that pre-treatment of activated macrophages with C15m and C17m decreases the amount and/or bioactivity of chemoattractants released by macrophages, and hence these peptides can significantly reduce continuing monocyte/macrophage recruitment to sites of inflammation.

Conditioned media from macrophages treated with C140+LPS/IFNγ, C15m+LPS/IFNγ, C17m+LPS/IFNγ and LPS/IFNγ alone were used in secondary chemotaxis assays to assess the potential pathophysiological repercussions associated with suppression of macrophage activation by C140 and its C-terminal peptides.

Cells ($0.5 \times 10^6$) were allowed to migrate towards chemoattractant (Chemerin peptides) or conditioned media in the bottom well of a modified Boyden chamber over 4 h. Serum free media (SFM) was used as a negative control. Filters were fixed in 4% formalin, then nuclei were stained with DAPI and visualised. Bar graphs indicate mean Migration Index (Chemoattractant % threshold area/SFM % threshold area) ±SEM for each treatment group. Each bar represents at least triplicate wells and 6 pictures taken per treatment. $p<0.001$ *; $p<0.01$  significance is relative to LPS/IFNγ conditioned media unless otherwise stated. AB refers to anti-murine Chemerin antibody.

As can be seen from the results presented in FIG. 5 macrophage-conditioned medium itself exhibited no chemotactic activity for macrophages, however, LPS/IFNγ-treated macrophage medium induced a dramatic increase in macrophage chemotaxis. Furthermore, macrophages exhibited reduced chemotaxis towards conditioned media from C140+LPS/IFNγ, C15m+LPS/IFNγ and C17m+LPS/IFNγ-treated macrophages, indicating the ability of C140, C15m and C17m to induce general suppression of a broad range of macrophage chemoattractants.

To exclude the possibility that Chemerin-treated supernatants harboured Chemerin-derived chemotactic proteins/peptides, supernatants were incubated with a neutralizing Chemerin antibody prior to assessment of macrophage migration. Chemerin did not appear to contribute to migration in Chemerin-treated supernatants.

Chemerin15-Mouse Suppresses Zymosan-Induced Peritonitis

Peritoneal inflammation can be induced by intraperitoneal injection of Zymosan particles (a yeast cell-wall component) which elicit an acute inflammatory response. Zymosan-induced peritonitis follows a well-described time-dependent accumulation of neutrophils then monocytes in mouse peritoneal cavities (for review see Lawrence T et al. Nat Rev Immunol. October 2002; 2(10):'787-795). This model has been utilized to demonstrate the pro-resolving properties of established mediators, Lipoxin A4 and annexin-1, which typically shorten the time course of inflammation with earlier restoration of tissue structure and function and suppression of neutrophil and monocyte extravasation. Previous experiments reported in the literature have used a range of doses of Zymosan A particles (10 μg-1 mg) (Taylor P R et al. Eur J Immunol. July 2005; 35(7):2163-2174; Arita M et al. J. Biol. Chem. Aug. 11, 2006 2006; 281(32):22847-22854).

Given the high chemotactic potential of chemerin and the inherent requirement for proteolysis, C-terminal synthetic peptide chemerin15 was used for in vivo characterization of anti-inflammatory effects in the sterile peritonitis model, since C15 is largely devoid of chemotactic activity (FIG. 3 and FIG. 4B) yet exerts anti-inflammatory effects that are comparable to those of proteolysed chemerin (Table 1).

With reference to the results shown in FIG. 6, this study used 10 μg per mouse (1-2 particles per resident macrophage) as this is thought to more closely represent a pathophysiological dose.

More specifically, male C57B16/J mice (8-12 weeks) were injected intra-peritoneally with 0.5 ml PBS or 0.5 ml Chemerin15-mouse (0.32 ng/kg) followed by injection with 0.5 ml PBS or Zymosan ($2 \times 10^6$ particles per cavity) an hour later. After 4 hours animals were sacrificed and peritoneal cavities washed with 5 ml PBS-3 mM EDTA. Total cell counts were obtained using Trypan blue exclusion test. For determination of cellular composition (Neutrophils vs mononuclear phagocytes), cells were blocked with 2.4G2 mAB for 5 mins and stained with PE-conjugated anti-mouse Ly-6G and FITC-conjugated anti-mouse 7/4 mAB for 10 mins. Cells were fixed in 1% formaldehyde prior to FACS analysis with CellQuest software. Gates were constructed around two populations, the neutrophils (N; $7/4^{high}$, Ly-6G$^{high}$) and inflammatory monocytes (Mo; $7/4^{high}$). C15 refers to Chemerin15-mouse. Z refers to Zymosan. $p<0.01$ **; $p<0.05$ * relative to Zymosan-treated.

Neutrophil ($7/4^{high}$, Ly-6G$^{high}$), monocyte ($7/4^{high}$, Ly-6G$^{low}$) and resident macrophage populations ($7/4^{low}$, Ly-6G$^{low}$) were determined according to Gordon S and Taylor P R Nat Rev Immunol. 2005; 5(12):953; Taylor P R et al. Eur J Immunol. August 2003; 33(8):2090-2097; and Taylor P R et al. Eur J Immunol. July 2005; 35(7):2163-2174.

The result of this study show that mice treated with C15m at a dose of 0.32 ng/kg (8 pg/mouse) exhibited reduced Zymosan-elicited monocyte and neutrophil recruitment by 42% and 52%, respectively (FIG. 6). Levels of TNFα were also reduced in mice treated with C15m.

The above result was further investigated. To determine the anti-inflammatory properties of the C15 peptide in vivo a time-course experiment was performed extending over 48 h. Neutrophil (7/4high, Ly-6Ghigh) and monocyte (7/4high, Ly-6Glow) populations in peritoneal lavage fluid were determined by FACS analysis according to published protocols (Taylor, P. R. et al., (2005). *Eur J Immunol* 35:2163-2174; Taylor, P. R., (2003). *Eur J Immunol* 33:2090-2097). Administration of zymosan into the mouse peritoneal cavity produced a time-dependent extravasation of inflammatory cells into the peritoneal cavity, which followed the typical profile of an acute inflammatory response (FIG. 7A-B, solid line). Neutrophils were the first leukocytes to infiltrate the cavity, detectable at 2 h post-zymosan with peak neutrophilia occurring at 4 h ($1.95 \times 10^6$ cells). Monocyte influx into the inflamed peritoneal cavity was first detectable after 4 h ($0.69 \times 10^6$ cells), peaking at 24 h post-zymosan injection ($1.25 \times 10^6$ cells) and declining thereafter. Pre-treatment with C15 at a dose of 8 pg/mouse (≈0.32 ng/kg) 1 h prior to zymosan challenge brought the peak neutrophilia forward to 2 h with approximately 50% the magnitude of that of zymosan challenged mice (reduced from $1.25 \times 10^6$ to $0.62 \times 10^6$ cells; FIG. 7A, dotted line). Significant suppression of neutrophil infiltration by C15 was seen at 2 h, (50%), 4 h (66%) and 24 h (50%). A single dose of 8 pg of C15 peptide was also effective in reducing the number of peritoneal monocytes in inflamed cavities at all time points, with greater than 60% suppression seen at 4 h (63%), 8 h (61%), and 48 h (64%; FIG. 7B, dotted line). The rate of monocyte infiltration was highest 2-4 h post-zymosan injection ($0.51 \times 10^6$/h) and administration of C15 reduced the rate of influx into the inflamed cavity ($0.18 \times 10^6$/h). A single dose of C15 peptide prior to zymosan-challenge therefore provided significant protection against zymosan-induced peritoneal inflammation over the 48 h duration of the experiment.

The time-course experiment identified the 4 h post-zymosan time point as an appropriate point for validation of C15's anti-inflammatory activity. In this study a single dose of C15 produced a dose-dependent reduction in zymosan-elicited neutrophil and monocyte recruitment which was maximal at 8 pg/mouse C15 (≈0.32 ng/kg; FIGS. 7C-E and 16A-B), although significant anti-inflammatory effects were seen with a dose as low as 4 pg/mouse (≈0.16 ng/kg; FIG. 14B). When C15 was administered 1 h prior to zymosan-challenge neutrophil numbers were reduced from $1.9 \times 10^6$ to $0.78 \times 10^6$ (63% decrease; FIG. 7C) and monocyte levels from $0.69 \times 10^6$ to $0.30 \times 10^6$ (62% decrease; FIG. 7D, representative FACS plots at the 4 h time point are shown in FIG. 7E). C15 administration also markedly diminished the expression of pro-inflammatory cytokines in peritoneal lavage fluid at 4 h, including TNFα (51%), IL-1β (67%), IL-6 (67%), MCP-1 (59%), and KC (38%; FIG. 7F). The control peptides C15-S and C15-M which were devoid of in vitro anti-inflammatory activity (Table 1) were also found to not be protective when administered in vivo at the same dose and time as C15 as judged by monocyte and neutrophil levels (FIG. 7C-D). Significant suppression of monocyte ($0.69 \times 10^6$ to $0.42 \times 10^6$ cells; 42% decrease) and neutrophil recruitment ($1.9 \times 10^6$ to $0.83 \times 10^6$ cells; 60% decrease) was still seen 4 h post-zymosan when the same dose of C15 was given 2 h post-zymosan injection (FIG. 7G). This demonstrates that C15 can reduce neutrophil and monocyte recruitment in an already established inflammatory setting, providing another indication that C15/C15-derivatives may represent attractive pharmacophores targeting inflammatory pathologies.

Blockade of Endogenous Chemerin Species Exacerbates Peritoneal Inflammation

A potential endogenous role for chemerin and chemerin-derived peptides was investigated by injecting mice i.p with a neutralizing polyclonal anti-rmChemerin antibody (ChAb) or a control IgG 1 h prior to a 4 h or 24 h zymosan challenge. It was previously found that ChAb but not control IgG was capable of inhibiting C15 and chemerin-induced MΦ chemotaxis and anti-inflammatory effects in vitro (FIG. 8A-B). In vivo it was found that neutralization of endogenous chemerin species resulted in a 63% rise in peritoneal neutrophil numbers and a 45% increase in monocyte levels at the 4 h time point relative to control IgG-treated mice and a 170% and 86% increase in peritoneal neutrophil and monocyte levels 24 h after zymosan injection (FIG. 8C-D). This exacerbation of peritoneal inflammation over a 24 h period suggests an important endogenous anti-inflammatory role for chemerin species in vivo.

Chemerin15-Mouse Alone does not Induce Neutrophil or Macrophage Recruitment but does Reduce TNFα Levels Male C57B16/J mice (8-12 weeks) were injected intra-peritoneally with 0.5 ml PBS or 0.5 ml Chemerin15-mouse (0.32 ng/kg). After 4 hours three animals per treatment group were sacrificed and peritoneal cavities washed with 5 ml PBS-3 mM EDTA. Total cell counts were obtained using Trypan blue exclusion test. For determination of cellular composition (Neutrophils vs mononuclear phagocytes), cells were blocked with 2.4G2 anti-FcgRII/III mAB for 5 mins and stained with PE-conjugated anti-mouse Ly-6G and FITC-conjugated anti-mouse 7/4 mAB for 10 mins. Cells were fixed in 1% formaldehyde prior to FACS analysis with CellQuest software. Gates were constructed around two populations, the neutrophils (N; $7/4^{high}$, Ly-6G$^{high}$) and inflammatory monocytes (Mo; 7/4$^{high}$, Ly-6G$^{low}$). C15 refer to Chemerin15-mouse. p<0.01 ** relative to PBS-treated. Ns refers to no statistically significant difference p>0.05.

As can be seen from the results in FIG. 9, 0.32 ng/kg of C15m does not cause monocyte or neutrophil migration. However, a significant reduction in TNFα is observed.

This model, studying sterile peritonitis in mice is widely used in experimental medicine and pharmacology, and represents mild inflammation caused by moderate tissue trauma or infection. The results indicate that C15m is capable of achieving a therapeutic anti-inflammatory effect.

Modified Chemerin13-Human Suppresses Rantes and TNFα Transcript Expression in Murine Macrophages Murine peritoneal macrophages (PMθ) were cultured under various conditions: Untreated, LPS (100 ng/ml) and IFNγ (20 ng/ml) for 15 h, modified Chemerin13-human (1 nM) pre-treatment for 1 h then LPS/IFNγ for 15 h. The bar graphs show the mean expression of cytokine transcript determined by qRT-PCR and normalised to housekeeper, hypoxanthine phosphoribosyltransferase, HPRT. Experiments were performed with triplicate determinations for each treatment, n=1 independent experiments. p<0.01 **; p<0.05 * relative to LPS/IFNγ-treated samples unless otherwise stated. The sequence of the modified C13h peptide is NH$_2$-FHSFYF-PGQFAFS-COOH (Seq ID No: 43)—in this sequence the N terminal P in C13h has been replaced with the amino acid F, and the peptide is therefore referred to as modified C13h.

As can be seen from the result in FIG. 10, modified C13h significantly reduced expression of TNFα and RANTES.

Chemerin 17-Mouse does not Affect C140 Induced Macrophage Chemotaxis

PMθ were recruited following a 4 day peritoneal stimulation with BioGEL beads. Peritoneal cavities of male C57B16/J mice were lavaged with 5 ml PBS-2 mM EDTA. Cells were centrifuged and resuspended in RPMI supplemented with 0.5% BSA and 25 mM Hepes. Cells (0.5×10$^6$) were allowed to migrate towards chemoattractant (C140, C17m or C17m+C140) in the bottom well over 4 h. Filters were fixed in 4% formalin, then nuclei were stained with DAPI and visualised. Serum free media was used as a negative control (−/−). Cells were preincubated with Pertussis toxin (PTX) for 30 mins before the chemotaxis assay. The bar graphs in FIG. 11 show the mean Migration Index±SEM for each treatment group. Each bar represents at least triplicate wells and at least 3 pictures taken per treatment. p<0.001 *; p<0.01 ; p<0.05 * relative to SFM treated wells unless otherwise stated.

The results in FIG. 11 show that co-administration of C17m with C140 did not appear to affect macrophage migration to C140.

Chemerin15-Mouse and Chemerin17-Mouse Suppress TNFα Secretion by Murine Macrophages Stimulated with Zymosan PMθ were cultured under various conditions: Untreated; Zymosan for 15 h; Chemerin (1 pM) pre-treatment for 1 h+Zymosan for 15 h. The bar graphs show mean expression of TNFα as determined by ELISA±SEM. Experiments were performed with triplicate determinations for each treatment. Representative data from three independent experiments employing cells from different donors are shown in FIG. 12. p<0.001 *; p<0.01  relative to Zymosan-treated samples. Dexa refers to dexamethasone (1 mM), nd refers to below the lower limit of detection (0.25 ng/ml).

As can be seen, treatment with C15m (1 pM) and C17m (1 pM) suppressed Zymosan-induced TNF expression (C15m; 21%, C17m; 30%). C15m and C17m therefore suppress macrophage activation induced by both bacteria (LPS) and yeast (Zymosan A).

Checkerboard Analysis Demonstrates that Chemerin140 and Chemerin15-Mouse Induce Macrophage Chemotaxis not Chemokinesis Checkerboard analysis allows differentiation between chemotaxis and chemokinesis. Chemotaxis is indicated by migration toward a higher concentration of chemoattractant in the lower well. Chemokinesis refers to increased non-directional cell movement and occurs regardless of the concentration gradient present. Checkerboard analysis was performed by pre-incubating cells with C140 (10-500 pM) or C15m (10-1000 pM) and allowing them to migrate towards C140 (10-1000 pM) or C15m (10-1000 pM), respectively in the lower well to form a checkerboard of concentrations.

More specifically, PMθ were recruited following a 4 day peritoneal stimulation with BioGEL beads. Peritoneal cavities of male C57B16/J mice were lavaged with 5 ml PBS-2 mM EDTA. Cells were centrifuged and resuspended in RPMI supplemented with 0.5% BSA and 25 mM Hepes. Cells (0.5×10$^6$) were incubated with C140 or C15m for 30 mins before the chemotaxis assay and then allowed to migrate towards chemoattractant in the bottom well over 4 h. Filters were fixed in 4% formalin, then nuclei were stained with DAPI and visualised. Serum free media (SFM) was used as a negative control (−/−) and the CC chemokine RANTES as a positive control (25 ng/ml). The bar graphs in FIG. 13 show the mean Migration Index±SEM for each treatment group. Each bar represents at least triplicate wells and at least 3 pictures taken per treatment. p<0.001 *** relative to SFM-treated wells.

It was found that C140 and C15m elicit true chemotaxis rather than chemokinesis as migration into the lower well of the Boyden chamber only occurred when a higher concentration of chemoattractant was placed in it and not when placed on the upper side of the filter.

C15m is shown to be a much weaker inducer of macrophage chemotaxis the C140.

C15 Induces Macrophage Phagocytosis of Zymosan

For in vitro recognition of zymosan by macrophages, peritoneal exudate cells were isolated by lavage with ice-cold 2 mM EDTA in PBS from mice that had been treated intraperitoneally 4 d before with Biogel beads (2% w/v). Macrophages were plated in 24-well plates at a density of 2.5×10$^5$ cells per well in Optimem medium. Cells were washed three times with medium before the addition of Fluorescein isothiocyanate (FITC)-labeled zymosan (Invitrogen) in recognition assays at macrophage/particle ratios of 10:1 in the presence of either 0.1 pM, 1 pM, 10 pM, 100 pM or 1 nM Chemerin15. Vehicle=control sample without Chemerin15. FITC-zymosan uptake was followed by FACS analysis and is expressed as a relative recognition index i.e the ratio of %® cells uptaking zymosan×the ratio of geometric means C15 treated macrophages/geometric mean of macrophages treated with vehicle.

Figure 15:
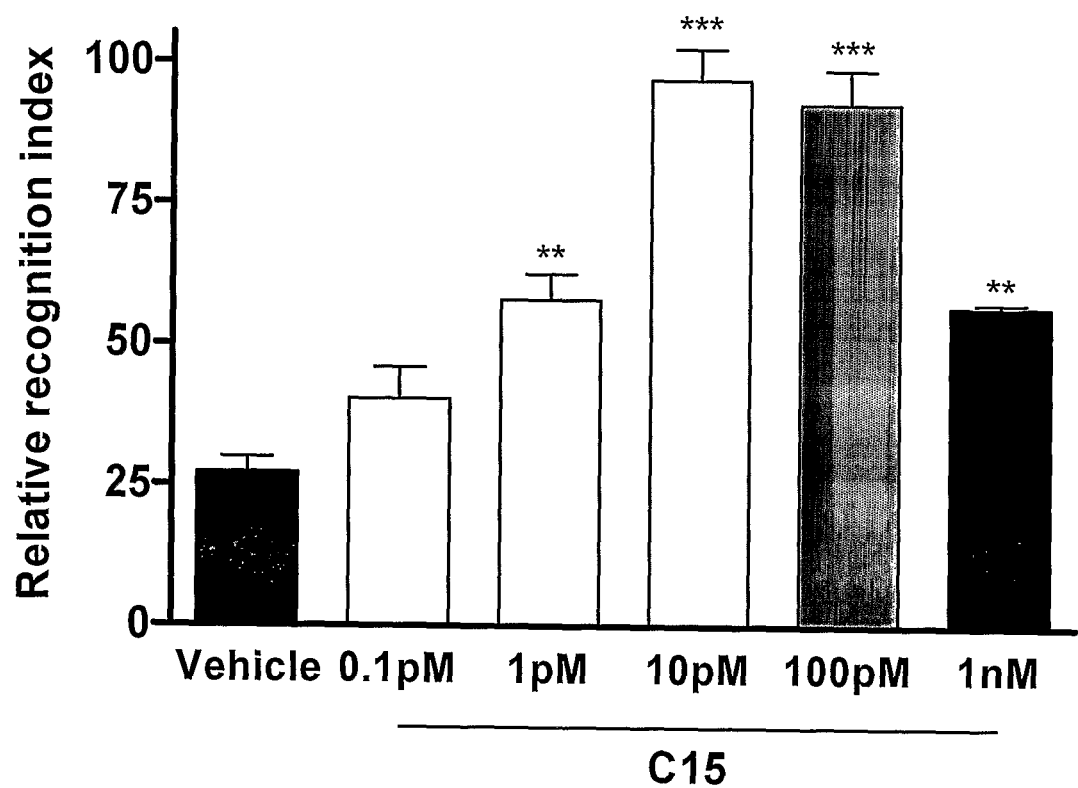

The results shown in FIG. 15 indicate that Chemerin15 induces macrophage phagocytosis of zymosan. The induction of macrophage phagocytosis is greatest at a Chemerin15 concentration of 10 pM. These results demonstrate that chemerin peptides may accelerate wound repair by increasing macrophage phagocytosis of apoptotic cells, cellular debris, pathogens and pathogen products.

Discussion

It is known that multiple mediators coordinate the initial events of acute inflammation. For example, lipid-derived eicosanoids, cytokines and chemokines regulate vascular alterations and inflammatory cell recruitment. Pro-inflammatory cytokines, including TNFα and IL-1γ activate signaling pathways in endothelial cells, resulting in upregulation of adhesion molecule expression, facilitating the capture of circulating leukocytes. The results presented above show that C-terminal peptides derived from Chemerin140 are able to suppress all of the components of the inflammatory response. The results also show that C-terminal peptides derived from Chemerin140 are able to reduce chemokines levels and could be used as a therapy for endotoxic shock.

All the peptides used in this study are Chemerin-derived, and display incredibly high potency ($10^{-12}$M) which ensures that these mediators join the ranks of complement-derived chemotaxin, C5a des-arg ($10^{-12}$M), formyl-Methionyl-Leucyl-Phenylalanine (fMLP; $10^{-11}$M), leukotriene B4 (LTB4; $10^{-11}$M), TNFα ($10^{-11}$M), LPS ($10^{-15}$M) and IL-1 ($10^{-14}$M). The applicant know of no pharmaceutical preparations that have been demonstrated to exhibit physiological effects at $10^{-11}$M-$10^{-15}$M. Indeed, dexamethasone is commonly administered at concentrations in the micromolar range in vitro and achieves 50% downregulation of monocyte and neutrophil influx in the Zymosan-induced peritonitis model at 30 μg/mouse (1.2 mg/kg). Chemerin15-mouse downregulated monocyte and neutrophil recruitment to a similar extent as 30 μg Dexamethasone. Chemerin15-mouse produces equivalent anti-inflammatory effects in this murine model of inflammation with a dose of only 8 pg per mouse (0.32 ng/kg).

Secondary chemotaxis assays allowed the chemotactic potential of supernatants from macrophage activation assays to be quantified, and the impact of Chemerin-mediated chemokine suppression on the chemotactic properties of the media to be determined. Analysis of these results revealed reduced macrophage migration towards supernatants from Chemerin+LPS/IFNγ-treated macrophages in comparison to LPS/IFNγ alone, indicating general suppression of a broad range of macrophage chemoattractants. The examples given demonstrate the limited or non-existent chemoattractant properties of Chemerin-derived anti-inflammatory peptides in comparison to C140.

In conclusion, the results show that C-terminal peptides of Chemerin exhibit extremely potent anti-inflammatory properties in vitro and in vivo.

Materials and Methods

Animals

All animal studies were conducted with local ethical approval and in accordance with the UK Home Office regulations (Guidance on the Operation of Animals, Scientific Procedures Act, 1986).

Antibodies and Reagents

Anti-human Chemerin, anti-murine Chemerin AB, hChemerin 137 (sequence ID no: 31, available from RandD as recombinant Glu21-Ser157), mChemerin 140 (Seq ID no: 34), anti-mRANTES Capture AB, anti-mRANTES Detection AB, mRANTES, mTNFα, anti-mTNFα Capture AB, anti-mTNFα Detection AB were purchased from R&D Systems. Chemerin peptides (C11m, C13m, C13h, C15m, C17m) were synthesised by biosynthesis (www.biosyn.com). Dexamethasone, Lipopolysaccharide (E. coli), Leupeptin were obtained from Sigma Aldrich. Interferon gamma (IFNγ) was purchased from Peprotech. OPD tablets were obtained from Dakocytomata, Streptavidin-HRP and StrepAv-HRP dilution buffer were purchased from Endogen. Luminex 6-plex kit (IL-12 p40, IL-1β, IL-6, MCP-1, TNFα, IL-10) was provided by Bio-rad and analysed using a Bio-rad bioanalyser and X software.

Inhibition of Macrophage Activation—Macrophage Activation Assay 1 ml 2% BioGEL polyacrylamide beads in sterile Phosphate-Buffered Saline (PBS) were injected intraperitoneally (ip) into C57B1/6J mice. Four days after ip BioGEL administration, mice were sacrificed by the CO, method according to Home Office guidelines. Peritoneal cavities were flushed with 10 ml sterile PBS-2 mM EDTA to harvest BioGEL-evoked/elicited cellular infiltrate. Suspensions of harvested cells were centrifuged at 1000×g for 5 mins at 4° C. The supernatants were discarded and cell pellets were resuspended in 6 mls OptiMEM medium supplemented with 2 mM Glutamine, 50 units/ml Penicillin and 50 μg/ml Streptomycin. Macrophages were quantified following incubation on ice for 5-10 mins with Turk's solution using a haemocytometer. Cell suspensions (2 mls; $1.5 \times 10^6$/well) were plated in six-well tissue culture plates (35 mm diameter: Costar, UK) and allowed to adhere for 2 hours at 37° C. in a humidified atmosphere containing 5% CO, to isolate macrophage populations by adherence. This gave greater than 95% purity assessed by cytospinning, staining of cells with Methylene Blue and Eosin and counting based on cellular morphology. Nonadherent cells (mainly granulocytes) were discarded and wells were washed three times with sterile PBS to remove loosely adherent or dead cells. In order to evaluate potential suppression of macrophage activation and hence a reduction in the expression of pro-inflammatory mediators, macrophages ($1.5 \times 10^6$ cells/well) were pre-incubated with Chemerin peptides (C11m, C13m, C15m, C17m; $10^{-12}$-$10^{-8}$ M) or positive control (Dexamethasone; 1 μM) for 1 h and then challenged with LPS (100 ng/ml) and IFNγ (20 ng/ml) for 15 h. To determine PTX sensitivity and dependency upon proteolysis, cells were pre-incubated with PTX (200 ng/ml) or Leupeptin (15 μg/ml). Additional cells were treated with peptides alone. Supernatants were harvested and stored at −20° C. until use in Enzyme-Linked Immunosorbance Assays (ELISAs) and Luminex assays. Cells were lysed to allow extraction of total RNA by the TRIZOL method. Lysates were stored at −80° C. until RNA extraction following manufacturer's guidelines (Qiagen, RNeasy Mini Prep Kit).

Detection of Secreted Protein by ELISAs and Luminex

RANTES, Tumour necrosis factor (TNFα) and CCL9 concentrations in cell supernatants were assessed by ELISA. IL-12 p40, IL-10, IL-1β, TNFα, MCP-1 (Monocyte chemoattractant protein-1) and IL-6 levels were determined by Luminex multiplex bead assay (Bio-rad 6 plex assay). Lower limits of detection for ELISAs were 0.1-0.5 ng/ml and 10-50 pg/ml for Luminex assays.

RNA Preparation and RT-PCR

Total RNA was extracted using Qiagen RNeasy kits, reverse transcribed and subjected to qRT-PCR using the Sybr-Green method. Data was analysed using the 2-ΔΔCT method (Livak, K. J. & Schmittgen T. D. (2001), *Methods* 25:402-408).

Chemotaxis Assay

Cell migration was assessed by use of transwell membranes (ChemoTX, 6-mm diameter, 8-μm pore size). Briefly, BioGEL-elicited cells were harvested and placed on transwell membranes (250 000 cells/membrane in RPMI supplemented with 25 mM Hepes and 0.1% bovine serum albumin. Cells were allowed to migrate toward Chemerin peptides (1 pM-100 nM) for 4 h. Signal transduction via G protein-coupled receptors was blocked by preincubating cells with pertussis toxin (PTX, 200 ng/ml, Sigma-Aldrich) for 30 mins before placing cells on transwell membranes. Migrated cells on the underside of membranes were fixed (3% formaldehyde) and stained with DAPI. Migration was quantified as total pixel count of DAPI stained nuclei under the confocal microscope (2 photos/membrane and a minimum of 3 replicate wells per treatment). Images were analyzed using Metamorph Offline software to determine percentage threshold areas (TA) occupied by migrated cells. Migration indices were obtained by dividing treatment TA by serum-free media TA. For secondary chemotaxis assays ChemoTx 3-mm diameter, 8-μm pore membranes were used with 50 000 cells/membrane.

Murine Peritonitis

C57BL6/J mice were administered 500 μl Chemerin15-mouse (0.32 ng/kg) or vehicle alone (sterile PBS) i.p. 1 h before administration of 500 μl 10 μg Zymosan A i.p. After 4 h and humane sacrifice, peritoneal exudates were collected by peritoneal lavage with 5 ml of sterile PBS-3 mM EDTA. Cell-free lavage fluid was obtained for use in ELISAs and exudate cells were prepared for analyses described below.

Differential Leukocyte Counts and FACS Analysis

C57BL6/J mice were administered 500 μl Chemerin15 (0.32 ng/kg) or vehicle (PBS) i.p. 1 h before administration of 500 μl 10 μg Zymosan A i.p. After 2 h, 4 h, 8 h, 16 h, 24 h and 48 h and humane sacrifice. Aliquots of lavage cells were prepared for determination of total and differential leukocyte counts. For determination of cellular composition (PMN vs mononuclear cells), cells were blocked with anti-mouse 2.42G FcμII/III (0.5 μg/0.1×10$^6$ cells) for 10 min and stained (10 min) with FITC-conjugated anti-mouse 7/4 and PE-conjugated anti-mouse Ly-6G (0.5 μg/0.5×10$^6$ cells; clones rmC5-3 and RB6-8C5, respectively from BD Pharmingen). Cells were analysed on a FACSCalibur flow cytometer with CellQuest software. For each sample, a minimum of 10,000 events was acquired. Gates were constructed around three populations, the neutrophils (7/4$^{high}$, Ly-6G$^{high}$), monocytes (7/4$^{high}$, Ly-6G$^{low}$) and resident macrophages (7/4$^{low}$, Ly-6G$^{low}$). The percentage of total events in each population were measured. In addition, cell-free lavage fluid was collected for use in ELISA and Luminex assays.

Statistics

Student's t test and one way ANOVA were performed using GraphPad Prism software.

---

The invention claimed is:

1. A method of treating or ameliorating inflammation in a subject in need thereof comprising administering to the subject an isolated peptide derived from the C-terminal end of a Chemerin protein, wherein the isolated peptide comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 37 or 38.

2. The method of claim 1, wherein the isolated peptide is administered at a dose of between about 10 pg/kg and about 1 mg/kg.

3. The method of claim 1, wherein the isolated peptide is acetylated, acylated, alkylated, or glycosylated.

4. The method of claim 1, wherein the isolated peptide consists of the sequence of amino acids of SEQ ID NO:19.

5. A medical device, wound dressing or bandage impregnated with an isolated peptide derived from the C-terminal end of a Chemerin protein, wherein the isolated peptide comprises a sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 37 or 38.

6. The medical device, wound dressing or bandage of claim 5, wherein the isolated peptide is acetylated, acylated, alkylated, or glycosylated.

7. The medical device, wound dressing or bandage of claim 5, wherein the isolated peptide consists of the sequence of amino acids of SEQ ID NO:19.

8. A pharmaceutical composition comprising an isolated peptide consisting of the sequence of amino acids of SEQ ID NO: 1, 2, 3, 4, 5, 6, 7, 8, 9, 10, 11, 12, 13, 14, 15, 16, 17, 19, 20, 22, 23, 24, 25, 26, or 27 and a pharmaceutically acceptable diluent, carrier or excipient.

9. The composition of claim 8, wherein the isolated peptide is acetylated, acylated, alkylated, or glycosylated.

10. The composition of claim 8, wherein the isolated peptide consists of the sequence of amino acids of SEQ ID NO:19.

11. A method of treating or ameliorating inflammation in a subject in need thereof comprising administering to the subject the composition of claim 8.

12. The method of claim 11, wherein the isolated peptide is administered by parenteral, subcutaneous, intravenous, intramuscular, intraperitoneal, intraarterial, intralesional, intrarticular, topical, oral, rectal, or nasal administration.

13. The method of claim 11, wherein the isolated peptide is administered by topical administration.

14. The method of claim 11, wherein the isolated peptide consists of the sequence of amino acids of SEQ ID NO:19.

15. An isolated peptide consisting of the sequence of amino acids of SEQ ID NO: 1, 2, 3, 4, 5, 6, 7, 8, 9, 10, 11, 12, 13, 14, 15, 16, 17, 19, 20, 22, 23, 24, 25, 26, or 27.

16. The isolated peptide of claim 15, wherein the isolated peptide is acetylated, acylated, alkylated, or glycosylated.

17. The isolated peptide of claim 15 consisting of the sequence of amino acids of SEQ ID NO:19.

18. An isolated peptide consisting of the sequence of amino acids of SEQ ID NO:19.

19. A pharmaceutical composition comprising an isolated peptide consisting of the sequence of amino acids of SEQ ID NO:19 and a pharmaceutically acceptable diluent, carrier or excipient.

20. A method of treating or ameliorating inflammation or reducing the level of one or more inflammatory mediators in a subject in need thereof comprising administering to the subject the composition of claim 19.

21. A method of treating or ameliorating inflammation or reducing the level of one or more inflammatory mediators in a subject in need thereof comprising administering to the subject an isolated peptide comprising the sequence of SEQ ID NO: 19.

22. A medical device, wound dressing or bandage impregnated with an isolated peptide comprising the sequence of SEQ ID NO: 19.

* * * * *